(12) United States Patent
Schindler et al.

(10) Patent No.: US 6,809,089 B2
(45) Date of Patent: Oct. 26, 2004

(54) SULFONYLAMINOCARBOXYLIC ACID N-ARYLAMIDES AS GUANYLATE CYCLASE ACTIVATORS

(75) Inventors: Ursula Schindler, Bad Soden (DE); Karl Schoenafinger, Alzenau (DE); Hartmut Strobel, Liederbach (DE)

(73) Assignee: Aventis Pharma Deutschland GmbH, Frankfurt am Main (DE)

(*) Notice: Subject to any disclaimer, the term of this patent is extended or adjusted under 35 U.S.C. 154(b) by 60 days.

(21) Appl. No.: 10/349,907

(22) Filed: Jan. 24, 2003

(65) Prior Publication Data

US 2003/0171352 A1 Sep. 11, 2003

Related U.S. Application Data

(63) Continuation of application No. 09/743,199, filed as application No. PCT/EP99/04427 on Jun. 25, 1999, now Pat. No. 6,548,547.

(30) Foreign Application Priority Data

Jul. 8, 1998 (DE) .......................................... 19830431

(51) Int. Cl.⁷ ........................ A61K 31/33; A61K 31/18; A61K 31/16; C07C 69/76; C07C 409/24

(52) U.S. Cl. ........................ 514/183; 514/604; 514/613; 560/8; 562/6; 562/582; 564/84; 564/123

(58) Field of Search ................................. 514/183, 604, 514/613; 560/8; 562/6, 582; 564/84, 123, 585, 256

(56) References Cited

U.S. PATENT DOCUMENTS

| | | | |
|---|---|---|---|
| 4,880,804 A | 11/1989 | Carini et al. | |
| 5,077,300 A | 12/1991 | Maienfisch et al. | |
| 5,081,125 A | 1/1992 | Maienfisch et al. | |
| 5,447,939 A | * 9/1995 | Glasky et al. | ............... 514/310 |
| 6,335,334 B1 | 1/2002 | Schindler et al. | |
| 6,548,547 B1 | * 4/2003 | Schindler et al. | ........... 514/604 |
| 2002/0061887 A1 | 5/2002 | Schindler et al. | |

FOREIGN PATENT DOCUMENTS

| | | |
|---|---|---|
| DE | 35 23 705 | 1/1987 |
| EP | 0 253 310 A2 | 1/1988 |
| EP | 0 324 377 A2 | 7/1989 |
| EP | 0 347 168 A1 | 12/1989 |
| EP | 0 420 804 A2 | 4/1991 |
| EP | 0 420 805 A2 | 4/1991 |
| EP | 0 449 699 A2 | 10/1991 |
| EP | 0 530 702 A1 | 3/1993 |
| EP | 0 947 500 A1 | 10/1999 |
| FR | 1579473 | 7/1969 |
| GB | 865735 | 4/1961 |
| GB | 1198301 | 8/1970 |
| WO | 9827053 | * 6/1998 |
| WO | WO 98/27053 | 6/1998 |

OTHER PUBLICATIONS

Prickaerts et al (PubMed Abstract 12127092, also cited as Neuroscience, 113/2,251–61(2002).*

Yen et al, PubMed Abstract 1772327, also cited as Arch. Int. Pharmacodyn Ther. 310,162–74(1991).*

U.S. patent application Ser. No. 09/743,199, Schindler et al., filed Mar. 8, 2001.

John V. Duncia et al., "The Discovery of Potent Nonpeptide Angiotensin II Receptor Antagonists: A New Class of Potent Antihypertensives," J. Med. Chem., 1990, vol. 33, pp. 1312–1329.

A. M. El–Nagger et al., "Synthesis and Biological Activity of Some New 4–(Aminoacyl)Aminopyridines and 2–(Aminoacyl)Aminopyrimidine Derivatives," Pol. J. Chem., 1982, pp. 1279–1285.

L. Gera et al., "Stereochemical Studies, XXXII, Acid Amides of Potential Pharmacological Activity, IV," Acta Chim. Hung, 99 (2): 175–192 (1979).

Louis J. Ignarro, "Regulation of Cytoslic Guanylyl Cyclase by Porphyrins and Metalloporphyrins," Advances in Pharmacology, vol. 26, 1994, pp. 35–64.

Feng–Nien Ko et al.,"YC–1, A Novel Activator of Platelet Guanylate Cyclase," Blood, vol. 84, No. 12, Dec. 15, 1994, pp. 4226–4233.

(List continued on next page.)

Primary Examiner—Richard L. Raymond
Assistant Examiner—Sudhaker B. Patel
(74) Attorney, Agent, or Firm—Fennigan, Henderson, Farabow, Garrett & Dunner, L.L.P.

(57) ABSTRACT

The present invention relates to compounds of the formula I

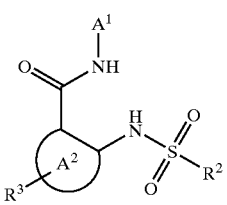

in which $A^1$, $A^2$, $R^2$ and $R^3$ have the meanings indicated in the claims, which are valuable pharmaceutical active compounds for the therapy and prophylaxis of diseases, for example of cardiovascular disorders such as high blood pressure, angina pectoris, cardiac insufficiency, thromboses or atherosclerosis. The compounds of the formula I have the ability to modulate the endogenous production of cyclic guanosine monophosphate (cGMP) and are generally suitable for the therapy and prophylaxis of disease states which are associated with a disturbed cGMP balance. The invention relates to the use of compounds of the formula I for the therapy and prophylaxis of the designated disease states and for the production of pharmaceuticals therefor, novel compounds of the formula I, pharmaceutical preparations comprising them and processes for their preparation.

9 Claims, No Drawings

OTHER PUBLICATIONS

Helen G. McFadden et al., "Synthesis of Pyrazoles and Pyrazolo[1,5-α]pyrimidines from 3-Arylsulfonylaminoacrylates," Aust. J. Chem., vol. 46, 1993, pp. 873–886.
Alexander Mülsch et al., "Purification of Heme–Containing Soluble Guanylyl Cyclase," Methods in Enzymology, vol. 195, 1991, pp. 377–383.
Douglas J. Pettibone et al., "A Structurally Novel Stimulator of Guanylate Cyclase With Long–Lasting Hypotensive Activity in the Dog," European Journal of Pharmacology, vol. 116, 1985, pp.307–312.
Yoshinori Tominaga et al., "Synthesis of Quinoline Derivatives Using Ketene Dithioacetals," J. Heterocycl. Chem., vol. 27, 1990, pp. 1217–1225.
D. L. Vesley, "B Complex Vitamins Activate Rat Guanylate Cyclase and Increase Cyclic GMP Levels," European Journal of Clinical Investigation, vol. 15, 1985, pp. 258–262.
David L. Vesley, "Phencyclidine Stimulates Guanylate Cyclase Activity," Biochemical and Biophysical Research Communications, vol. 88, No. 4, Jun. 27, 1979, pp. 1244–1248.
Pancras C. Wong et al., "Nonpeptide Angiotensin II Receptor Antagonists," Hypertension, vol. 15, No. 6, Part 2, Jun. 1990, pp. 823–834.
Chin–Chung Wu et al., "YC–1 Inhibited Human Platelet Aggregation Through NO–independent Activation of Soluble Guanylate Cyclase," British Journal of Pharmacology (1995), 116, 1973–1978.
Sheu–Meei Yu et al., "Vasorelaxant Effect of Isoliquiritigenin, A Novel Soluble Guanylate Cyclase Activator, In Rat Aorta," British Journal of Pharmacology (1995), 114, 1587–1594.
Cheu M. Yu et al., "Mechanism of Anti–Proliferation Caused by YC–1, An Indazole Derivative, In Cultured Rat A10 Vascular Smooth–muscle Cells," Biochem J. (1995), 306, 767–792.
Morrison & Boyd, Organic Chemistry, pp. 966–967 (1983).
Chemical Abstracts, vol. 70, Abstract No. 77 907.
Chemical Abstracts, vol. 74, Abstract No. 99 956.
Chemical Abstracts, vol. 76, Abstract No. 33 659.
Chemical Abstracts, vol. 77, Abstract No. 126 528.
Chemical Abstracts, vol. 77, Abstract No. 164 616.
Chemical Abstracts, vol. 79, Abstract No. 18 616.
Chemical Abstracts, vol. 81, Abstract No. 91 449.
Chemical Abstracts, vol. 99, Abstract No. 157 667.
Chemical Abstracts, vol. 100, Abstract No. 209 423.
Chemical Abstracts, vol. 102, Abstract No. 70 111.
Chemical Abstracts, vol. 104, Abstract No. 33 896.
Chemical Abstracts, vol. 104, Abstract No. 177 628.
Chemical Abstracts, vol. 106, Abstract No. 138 322.
Chemical Abstracts, vol. 106, Abstract No. 152 850.
Chemical Abstracts, vol. 115, Abstract No. 158 666.
Chemical Abstracts, vol. 116, Abstract No. 207 806.
Chemical Abstracts, vol. 116, Abstract No. 228 237.
Chemical Abstracts, vol. 116, Abstract No. 245 151.
Chemical Abstracts, vol. 117, Abstract No. 39 809.
Chemical Abstracts, vol. 119, Abstract No. 105 757.
Chemical Abstracts, vol. 119, Abstract No. 116 978.
Chemical Abstracts, vol. 119, Abstract No. 180 796.
Chemical Abstracts, vol. 120, Abstract No. 560.
Chemical Abstracts, vol. 122, Abstract No. 136 749.
Chemical Abstracts, vol. 126, Abstract No. 277 494.

* cited by examiner

SULFONYLAMINOCARBOXYLIC ACID N-ARYLAMIDES AS GUANYLATE CYCLASE ACTIVATORS

This application is a continuation of prior U.S. application Ser. No. 09/743,199, filed on Mar. 8, 2001 now U.S. Pat. No. 6,548,547, (the contents of which are incorporated by reference herein), which is a national stage filing under 35 U.S.C. § 371 of international application no. PCT/EP99/04427, filed on Jun. 25, 1999.

The present invention relates to compounds of the formula I

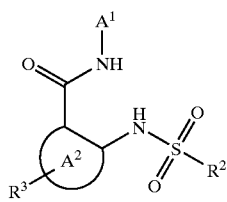

in which $A^1$, $A^2$, $R^2$ and $R^3$ have the meanings indicated below, which are valuable pharmaceutical active compounds for the therapy and prophylaxis of diseases, for example of cardiovascular disorders such as high blood pressure, angina pectoris, cardiac insufficiency, thromboses or atherosclerosis. The compounds of the formula I have the ability to modulate the endogenous production of cyclic guanosine monophosphate (cGMP) and are generally suitable for the therapy and prophylaxis of disease states which are associated with a disturbed cGMP balance. The invention relates to the use of compounds of the formula I for the therapy and prophylaxis of the designated disease states and for the production of pharmaceuticals therefor, novel compounds of the formula I, pharmaceutical preparations comprising them and processes for their preparation.

cGMP is an important intracellular messenger, which elicits a number of pharmacological effects by means of the modulation of cGMP-dependent protein kinases, phosphodiesterases and ion channels. Examples are smooth muscle relaxation, the inhibition of platelet activation and the inhibition of smooth muscle cell proliferation and leukocyte adhesion. cGMP is produced by particulate and soluble guanylate cyclases as a response to a number of extracellular and intracellular stimuli. In the case of the particulate guanylate cyclases, the stimulation essentially takes place by means of peptidic messenger substances, such as the atrial natriuretic peptide or the cerebral natriuretic peptide. The soluble guanylate cyclases (sGC), which are cytosolic, heterodimeric heme proteins, however, are essentially regulated by a family of low molecular weight, enzymatically formed factors. The most important stimulant is nitrogen monoxide (NO) or a closely relates species. The importance of other factors such as carbon monoxide or the hydroxyl radical is still largely unclarified. The binding of NO to the heme with formation of a pentacoordinated heme-nitrosyl complex is discussed as an activation mechanism of activation by NO. The release associated therewith of the histidine which is bound to the iron in the basal state converts the enzyme into the activated conformation.

Active soluble guanylate cyclases are each composed of one α- and one β-subunit. Several subtypes of the subunits have been described, which differ from one another with respect to sequence, tissue-specific distribution and expression in various stages of development. The subtypes $\alpha_1$ and $\beta_1$ are mainly expressed in the brain and lung, while $\beta_2$ is especially found in liver and kidney. The subtype $\alpha_2$ was detected in human fetal brain. The subunits designated as $\alpha_3$ and $\beta_3$ were isolated from human brain and are homologous to $\alpha_1$ and $\beta_1$. More recent studies point to an $\alpha_{2i}$ subunit, which contains an insert in the catalytic domain. All subunits show great homology in the area of the catalytic domain. The enzymes presumably contain one heme per heterodimer, which is bonded via $\beta_1$-Cys-78 and/or $\beta_1$-His-105 and is part of the regulatory center.

The formation of guanylate cyclase-activating factors can be decreased under pathological conditions or increased degradation thereof can take place as a result of the increased occurrence of free radicals. The decreased activation of the sGC resulting therefrom leads, via the attenuation of the respective cGMP-mediated cell response, for example, to an increase in the blood pressure, to platelet activation or to increased cell proliferation and cell adhesion. As a result, the formation of endothelial dysfunction, atherosclerosis, high blood pressure, stable and unstable angina pectoris, thromboses, myocardial infarct, strokes or erectile dysfunction occurs. The pharmacological stimulation of the sGC offers a possibility for the normalization of cGMP production and thus allows the treatment or prevention of diseases of this type.

For the pharmacological stimulation of sGC, until now compounds have almost exclusively been used whose action is based on an intermediate release of NO, for example organic nitrates. The disadvantage of this method of treatment lies in the development of tolerance and reduction of activity and the higher dosage which therefore becomes necessary.

Various sGC stimulators which do not act via a release of NO have been described in a series of publications by Vesely. The compounds, which are mostly hormones, plant hormones, vitamins or, for example, natural substances such as lizard toxins, however, predominantly show only weak effects on cGMP formation in cell lysates (D. L. Vesely, Eur. J. Clin. Invest. 15 (1985) 258; D. L. Vesely, Biochem. Biophys. Res. Comm. 88 (1979) 1244). Stimulation of heme-free guanylate cyclase by protoporphyrin IX was detected by Ignarro et al. (Adv. Pharmacol. 26 (1994) 35). Pettibone et al. (Eur. J. Pharmacol. 116 (1985) 307) described a hypotensive action for diphenyliodonium hexafluorophosphate and attributed this to a stimulation of sGC. Isoliquiritiginin, which shows a relaxant action on isolated rat aortas, likewise activates sGC according to Yu et al. (Brit. J. Pharmacol. 114 (1995) 1587). Ko et al. (Blood 84 (1994) 4226), Yu et al. (Biochem. J. 306 (1995) 787) and Wu et al. (Brit. J. Pharmacol. 116 (1995) 1973) detected an sGC stimulating activity of 1-benzyl-3-(5-hydroxymethyl-2-furyl)indazole and demonstrated an antiproliferative and platelet-inhibiting action.

A number of sulfonylaminocarboxylic acid N-arylamides of the formula I are already known. Compounds of this type are used, for example, in the production of photographic materials (see, for example, Chemical Abstracts 119, 105 755; 116, 245 151 and 104, 177 628) and, for this purpose, then in general contain in the N-aryl group as substituents easily oxidizable groups such as, for example, two hydroxyl groups in the para-position to one another. For various compounds of the formula I, a pharmacological action has also already been described. Thus, for example, in DE-A-35 23 705, an anthelmintic action is described for a series of 2-phenylsulfonylaminobenzamides. Antiparasitic, antimicrobial or fungicidal actions of 2-sulfonylaminobenzoic acid N-(hetero)arylamides are also mentioned, for example, in EP-A-420 805 and in Chemical Abstracts 122, 136 749; 120, 560; 119, 116 978; 116, 228 237; 116, 207 806; 115, 158 666 and 106, 152 850. According to EP-A-347 168, certain compounds of the formula I having a phenyl pivalate structure are elastase inhibitors and can be used in the treatment of atherosclerosis or arthritis. In Chemical Abstracts 104, 33 896, a psychotropic action is described for certain 2-sulfonylaminobenzoic acid N-phenoxyphenylamides. Various 2-trifluoromethylsulfonylamino- and 2-methylsulfonylamino-substituted benzamides are described as angiotensin II receptor antagonists having antihypertensive activity in Hypertension 15 (1998) 823, J. Med. Chem. 33 (1990) 1312, EP-A-253 310, EP-A-324 377, EP-A-449 699, EP-A-530 702 and U.S. Pat. No. 4,880,804.

Surprisingly, it has now been found that the compounds of the formula I bring about strong guanylate cyclase activation, on account of which they are suitable for the therapy and prophylaxis of diseases which are associated with a low cGMP level.

The present invention thus relates to the use of compounds of the formula I

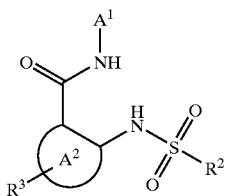

I in which
- $A^1$ is a radical from the group consisting of phenyl, naphthyl and heteroaryl, which can all be substituted by one or more identical or different radicals $R^1$;
- the ring $A^2$, which includes the carbon atoms which carry the groups CO—NH— and NH—SO$_2$R$^2$, is a benzene ring, a naphthalene ring, a saturated or partially unsaturated 3-membered to 7-membered carbocycle, a saturated, partially unsaturated or aromatic monocyclic 5-membered to 7-membered heterocycle which contains one or more ring heteroatoms from the group consisting of N, O and S, or a saturated, partially unsaturated or aromatic bicyclic 8-membered to 10-membered heterocycle which contains one or more ring heteroatoms from the group consisting of N, O and S;
- $R^1$ is halogen, aryl, CF$_3$, NO$_2$, OH, —O—(C$_1$–C$_7$)-alkyl, —O—(C$_2$–C$_4$)-alkyl-O—(C$_1$–C$_7$)-alkyl, —O-aryl, (C$_1$–C$_2$)-alkylenedioxy, NR$^5$R$^6$, CN, CO—NR$^5$R$^6$, COOH, CO—O—(C$_1$–C$_5$)-alkyl, heterocyclyl, CHO, CO—(C$_1$–C$_{10}$)-alkyl, CO-aryl or (C$_1$–C$_{10}$)-alkyl which can be substituted by one or more identical or different radicals $R^4$;
- $R^2$ is aryl, heterocyclyl, NR$^5$R$^6$ or (C$_1$–C$_{10}$)-alkyl which can be substituted by one or more identical or different radicals $R^4$;
- $R^3$ is one or more identical or different substituents from the group consisting of hydrogen, halogen, CF$_3$, OH, —O—(C$_1$–C$_{10}$)-alkyl, —O—(C$_1$–C$_7$)-alkyl-R$^7$, —O-aryl, SH, —S—(C$_1$–C$_{10}$)-alkyl, —S—(C$_1$–C$_7$)-alkyl-R$^7$, —S-aryl, (C$_1$–C$_3$)-alkylenedioxy, CN, NO$_2$, NR$^8$R$^9$, CO—NR$^5$R$^6$, COOH, CO—O—(C$_1$–C$_5$)-alkyl, heterocyclyl, S(O)$_n$—(C$_1$–C$_7$)-alkyl, S(O)$_n$-aryl, S(O)$_n$—NR$^5$R$^6$ and (C$_1$–C$_7$)-alkyl which can be substituted by one or more identical or different radicals $R^4$;
- $R^4$ is fluorine, OH, —O—(C$_1$–C$_{10}$)-alkyl, —O—(C$_1$–C$_7$)-alkyl-R$^7$, —O-aryl, SH, —S—(C$_1$–C$_{10}$)-alkyl, —S—(C$_1$–C$_7$)-alkyl-R$^7$, —S-aryl, —P(O)(O—(C$_1$–C$_5$)-alkyl)$_2$, —P(O)(OH)$_2$, CN, NR$^8$R$^9$, CO—NH$_2$, CO—NH—(C$_1$–C$_3$)-alkyl, CO—N((C$_1$–C$_3$)-alkyl)$_2$, COOH, CO—O—(C$_1$–C$_5$)-alkyl, heterocyclyl or oxo;
- $R^5$ is hydrogen, (C$_1$–C$_{10}$)-alkyl which can be substituted by one or more identical or different substituents $R^4$ and/or by aryl, or is aryl, heterocyclyl, CO—(C$_1$–C$_{10}$)-alkyl, CO-aryl, CO-heterocyclyl, SO$_2$—(C$_1$–C$_{10}$)-alkyl, SO$_2$-aryl or SO$_2$-heterocyclyl;
- $R^6$, independently of $R^5$, has one of the meanings indicated for $R^5$, or $R^5$ and $R^6$, together with the nitrogen atom to which they are bonded, form a 5-membered to 8-membered saturated or partially unsaturated ring which, in addition to the nitrogen atom carrying the groups $R^5$ and $R^6$, can also contain one or more further ring heteroatoms from the group consisting of N, O and S and which can be substituted by one or more identical or different substituents from the group consisting of fluorine, (C$_1$–C$_5$)-alkyl, (C$_1$–C$_3$)-hydroxyalkyl, —(C$_1$–C$_3$)-alkyl-O—(C$_1$–C$_4$)-alkyl, aryl, CF$_3$, OH, —O—(C$_1$–C$_7$)-alkyl, —O-aryl, —O—(C$_2$–C$_4$)-alkyl-O—(C$_1$–C$_7$)-alkyl, (C$_2$–C$_3$)-alkylenedioxy, NR$^8$R$^9$, CN, CO—NH$_2$, CO—NH—(C$_1$–C$_3$)-alkyl, CO—N((C$_1$–C$_3$)-alkyl)$_2$, COOH, CO—O—(C$_1$–C$_5$)-alkyl, CHO, CO—(C$_1$–C$_5$)-alkyl, S(O)$_n$—(C$_1$–C$_4$)-alkyl, S(O)$_n$—NH$_2$, S(O)$_n$—NH—(C$_1$–C$_3$)-alkyl, S(O)$_n$—N((C$_1$–C$_3$)-alkyl)$_2$, oxo, —(CH$_2$)$_m$—NH$_2$, —(CH$_2$)$_m$—NH—(C$_1$–C$_4$)-alkyl and —(CH$_2$)$_m$—N((C$_1$–C$_4$)-alkyl)$_2$, where in the substituent —(CH$_2$)$_m$—N((C$_1$–C$_4$)-alkyl)$_2$ the two alkyl groups can be linked by a single bond and then, together with the nitrogen atom carrying them, form a 5-membered to 7-membered ring which, in addition to the nitrogen atom and the carbon atoms, can additionally also contain an oxygen atom, a sulfur atom or a group NR$^5$ as a ring member;
- $R^7$ is OH, —O—(C$_1$–C$_7$)-alkyl, NH$_2$, —NH—(C$_1$–C$_4$)-alkyl or —N((C$_1$–C$_4$)-alkyl)$_2$, where in the substituent N((C$_1$–C$_4$)-alkyl)$_2$ the two alkyl groups can be linked by a single bond and then, together with the nitrogen atom carrying them, form a 5-membered to 7-membered ring which, in addition to the nitrogen atom and the carbon atoms can additionally also contain an oxygen atom, a sulfur atom or a group NR$^5$ as a ring member;
- $R^8$ is hydrogen or (C$_1$–C$_7$)-alkyl which can be substituted by one or more identical or different substituents from the group consisting of OH, —O—(C$_1$–C$_5$)-alkyl, NH$_2$, —NH—(C$_1$–C$_4$)-alkyl and —N((C$_1$–C$_4$)-alkyl)$_2$;
- $R^9$, independently of $R^8$, has one of the meanings of $R^8$ or is CO—(C$_1$–C$_4$)-alkyl;
- aryl is phenyl, naphthyl or heteroaryl, which can all be substituted by one or more identical or different substituents from the group consisting of halogen, (C$_1$–C$_5$)-alkyl, phenyl, tolyl, CF$_3$, NO$_2$, OH, —O—(C$_1$–C$_5$)-alkyl, —O—(C$_2$–C$_4$)-alkyl-O—(C$_1$–C$_3$)-alkyl, (C$_1$–C$_2$)-alkylenedioxy, NH$_2$, —NH—(C$_1$–C$_3$)-alkyl, —N((C$_1$–C$_3$)-alkyl)$_2$, NH—CHO, —NH—CO—(C$_1$–C$_5$)-alkyl, CN, CO—NH$_2$, CO—NH—(C$_1$–C$_3$)-alkyl, CO—N((C$_1$–C$_3$)-alkyl)$_2$, COOH, CO—O—(C$_1$–C$_5$)-alkyl, heterocyclyl, CHO, CO—(C$_1$–C$_5$)-alkyl, S(O)$_n$—(C$_1$–C$_4$)-alkyl, S(O)$_n$-phenyl, S(O)$_n$-tolyl, S(O)$_2$—NH$_2$, S(O)$_2$—NH—(C$_1$–C$_3$)-alkyl and S(O)$_2$—N((C$_1$–C$_3$)-alkyl)$_2$;

heteroaryl is the radical of a monocyclic 5-membered or 6-membered aromatic heterocycle or of a bicyclic 8-membered to 10-membered aromatic heterocycle, each of which contain one or more ring heteroatoms from the group consisting of N, O and S;

heterocyclyl is the radical of a monocyclic or polycyclic, 5-membered to 11-membered saturated or partially unsaturated heterocycle which contains one or more ring heteroatoms from the group consisting of N, O and S and which can be substituted by one or more identical or different substituents from the group consisting of fluorine, $(C_1-C_5)$-alkyl, OH, —O—$(C_1-C_5)$-alkyl, —O—$(C_2-C_4)$-alkyl-O—$(C_1-C_3)$-alkyl, $NH_2$, —NH—$(C_1-C_3)$-alkyl, —N$((C_1-C_3)$-alkyl$)_2$, CN, CO—$NH_2$, CO—NH—$(C_1-C_3)$-alkyl, CO—N$((C_1-C_3)$-alkyl$)_2$, COOH and CO—O—$(C_1-C_5)$-alkyl;

n is 0, 1 or 2;

m is 2, 3 or 4;

in all their stereoisomeric forms and mixtures thereof in all ratios, and their physiologically tolerable salts for the production of a medicament for the activation of soluble guanylate cyclase.

If groups or substituents can occur a number of times in the compounds of the formula I, they can all independently of one another have the indicated meanings and can each be identical or different.

Alkyl radicals can be straight-chain or branched. This also applies if they are contained in other groups, for example in alkoxy groups, alkoxycarbonyl groups or in amino groups, or if they are substituted. Examples of alkyl groups are methyl, ethyl, propyl, butyl, pentyl, hexyl, heptyl, octyl, nonyl, decyl, the n-isomers of these radicals, isopropyl, isobutyl, isopentyl, sec-butyl, tert-butyl, neopentyl, 3,3-dimethylbutyl. The term alkyl here is expressly also understood as meaning unsaturated alkyl radicals, i.e. alkyl radicals which contain one or more double bonds and/or one or more triple bonds, i.e. alkenyl radicals and alkynyl radicals. Examples of such radicals are the vinyl radical, the 2-propenyl radical (allyl radical), the 2-butenyl radical, the 2-methyl-2-propenyl radical, the ethynyl radical, the 2-propynyl radical (propargyl radical) or the 3-butynyl radical. Furthermore, the term alkyl here is expressly also understood as meaning radicals in which a cyclic system is formed by means of an internal ring closure, i.e., the term alkyl also includes saturated and partially unsaturated cycloalkyl radicals and cycloalkylalkyl radicals (alkyl substituted by cycloalkyl). Examples of such cycloalkyl radicals are cyclopropyl, cyclobutyl, cyclopentyl, cyclohexyl, cycloheptyl and cyclooctyl, which all can also be substituted, for example, by one or more identical or different $(C_1-C_4)$-alkyl radicals, in particular by methyl. Examples of such substituted cycloalkyl radicals are 4-methylcyclohexyl, 4-tert-butylcyclohexyl or 2,3-dimethylcyclopentyl. Furthermore, the term alkyl, if not stated otherwise, here expressly also includes both unsubstituted alkyl radicals and alkyl radicals which are substituted by one or more, for example one, two, three or four, identical or different aryl radicals. I.e., the term alkyl here is expressly also understood as meaning arylalkyl radicals, for example benzyl radicals, phenylethyl radicals or indanyl radicals.

A saturated or partially unsaturated 3-membered to 7-membered carbocycle representing the ring $A^2$ can be derived from the monocyclic parent structures cyclopropane, cyclobutane, cyclopentane, cyclohexane or cycloheptane. If the carbocycle is unsaturated, it can contain, for example, a double bond or, in the case of the 5-membered ring, 6-membered ring or 7-membered ring, also two double bonds, which can be isolated or conjugated. Double bonds can be situated in any desired positions with respect to the groups CO—NH— and NH—$SO_2$—$R^2$, thus, for example, a double bond can also be situated between the two ring carbon atoms which carry these two groups.

Phenyl radicals, naphthyl radicals and heterocyclic radicals, for example heteroaryl radicals, if not stated otherwise, can be unsubstituted or can carry one or more, for example one, two, three or four, identical or different substituents, which can be situated in any desired positions. If not stated otherwise, the substituents indicated in the definition of the group aryl, for example, can occur in these radicals as substituents. If, in compounds of the formula I, nitro groups are present as substituents, altogether only up to two nitro groups can be present in the molecule. If, for example, phenyl radicals, phenoxy radicals, benzyl radicals or benzyloxy radicals are present in aryl radicals such as, for example, phenyl radicals and/or in heterocyclic radicals as substituents, the benzene ring in these can also in turn be unsubstituted or can be substituted by one or more, for example one, two, three or four, identical or different radicals, for example by radicals from the group consisting of $(C_1-C_4)$-alkyl, halogen, hydroxyl, $(C_1-C_4)$-alkoxy, trifluoromethyl, cyano, hydroxycarbonyl, $((C_1-C_4)$-alkoxy) carbonyl, aminocarbonyl, nitro, amino, $(C_1-C_4)$-alkylamino, di-$((C_1-C_4)$-alkyl)amino and $((C_1-C_4)$-alkyl) carbonylamino.

In monosubstituted phenyl radicals, the substituent can be situated in the 2-position, the 3-position or the 4-position, in disubstituted phenyl radicals the substituents can be situated in the 2,3-position, 2,4-position, 2,5-position, 2,6-position, 3,4-position or 3,5-position. In trisubstituted phenyl radicals, the substituents can be situated in the 2,3,4-position, 2,3,5-position, 2,3,6-position, 2,4,5-position, 2,4, 6-position or 3,4,5-position. Tolyl (=methylphenyl) is 2-tolyl, 3-tolyl or 4-tolyl. Naphthyl can be 1-naphthyl or 2-naphthyl. In monosubstituted 1-naphthyl radicals, the substituent can be situated in the 2-position, the 3-position, the 4-position, the 5-position, the 6-position, the 7-position or the 8-position, in monosubstituted 2-naphthyl radicals in the 1-position, the 3-position, the 4-position, the 5-position, the 6-position, the 7-position or the 8-position. In higher substituted naphthyl radicals, for example 1-naphthyl radicals or 2-naphthyl radicals which carry two or three substituents, the substituents can also be situated in all possible positions.

Heteroaryl radicals, heterocyclyl radicals, heterocycles representing the ring $A^2$ and rings which are formed from two groups bonded to a nitrogen atom together with this nitrogen atom, are preferably derived from heterocycles which contain one, two, three or four identical or different ring heteroatoms, particularly preferably from heterocycles which contain one or two or three, in particular one or two, identical or different heteroatoms. If not stated otherwise, the heterocycles can be monocyclic or polycyclic, for example monocyclic, bicyclic or tricyclic. They are preferably monocyclic or bicyclic. The rings are preferably 5-membered rings, 6-membered rings or 7-membered rings. Examples of monocyclic and bicyclic heterocyclic systems from which radicals occurring in the compounds of the formula I can be derived are pyrrole, furan, thiophene, imidazole, pyrazole, 1,2,3-triazole, 1,2,4-triazole, 1,3-dioxole, 1,3-oxazole, 1,2-oxazole, 1,3-thiazole, 1,2-thiazole, tetrazole, pyridine, pyridazine, pyrimidine, pyrazine, pyran, thiopyran, 1,4-dioxin, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3- oxazepine, 1,3-thiazepine, indole, benzothiophene, benzofuran, benzothiazole, benzimidazole, quinoline, isoquinoline, cinnoline, quinazoline, quinoxaline, phthalazine, thienothiophenes, 1,8-naphthyridine and other naphthyridines, pteridine, or phenothiazine, all in each case in saturated form (perhydro form) or in partially unsaturated form (for example dihydroform and tetrahydro form) or in maximally unsaturated form if the forms concerned are known and stable. The suitable heterocycles thus also include, for example, the saturated heterocycles pyrrolidine, piperidine, piperazine, morpholine and thiomorpholine. The degree of saturation of heterocyclic groups is indicated in the individual definitions. Unsaturated heterocycles can contain, for example, one, two or three double bonds in the ring system. 5-Membered rings and 6-membered rings in monocyclic and polycyclic heterocycles can in particular also be aromatic.

The radicals derived from these heterocycles can be bonded via any suitable carbon atom. Nitrogen heterocycles which carry a hydrogen atom (or a substituent) on a ring nitrogen atom, for [lacuna] pyrrole, imidazole, pyrrolidine, morpholine, piperazine etc. can also be bonded via a ring nitrogen atom, in particular if the nitrogen heterocycle concerned is bonded to a carbon atom. A thienyl radical can be present, for example, as a 2-thienyl radical or 3-thienyl radical, a furan radical as a 2-furyl radical or 3-furyl radical, a pyridyl radical as a 2-pyridyl radical, 3-pyridyl radical or 4-pyridyl radical, a piperidine radical as a 1-piperidyl radical, 2-piperidyl radical, 3-piperidyl radical or 4-piperidyl radical, a thiomorpholine radical as a 2-thiomorpholinyl radical, 3-thiomorpholinyl radical or 4-thiomorpholinyl radical (=thiomorpholino radical). A radical bonded via a carbon atom, which is derived from 1,3-thiazole or from imidazole, can be bonded via the 2-position, the 4-position or the 5-position.

If not stated otherwise, the heterocyclic groups, such as, for example, heteroaryl radicals, can be unsubstituted or can carry one or more, for example one, two, three or four, identical or different substituents. The substituents in heterocycles can be situated in any desired positions, for example in the 3-position and/or in the 4-position and/or in the 5-position in a 2-thienyl radical or 2-furyl radical, in the 2-position and/or in the 4-position and/or in the 5-position in a 3-thienyl radical or 3-furyl radical, in the 3-position and/or in the 4-position and/or in the 5-position and/or in the 6-position in a 2-pyridyl radical, in the 2-position and/or in the 4-position and/or in the 5-position and/or in the 6-position in a 3-pyridyl radical, in the 2-position and/or in the 3-position and/or in the 5-position and/or in the 6-position in a 4-pyridyl radical. If not stated otherwise, the substituents which can occur are, for example, the substituents indicated in the definition of the group aryl, in the case of saturated or partially unsaturated heterocycles as further substituents also the oxo group and the thioxo group. Substituents on a heterocycle and substituents on a carbocycle can also form a ring, thus further rings can be fused to a ring system so that, for example, cyclopenta-fused, cyclohexa-fused or benzo-fused rings can be present. Suitable substituents on a substitutable nitrogen atom of a heterocycle are in particular, for example, unsubstituted $(C_1-C_5)$-alkyl radicals and aryl-substituted alkyl radicals, aryl radicals, acyl radicals such as $CO-(C_1-C_5)$-alkyl, or sulfonyl radicals such as $SO_2-(C_1-C_5)$-alkyl. Suitable nitrogen heterocycles can also be present as N-oxides or as quaternary salts having an anion derived from a physiologically tolerable acid as a counterion. Pyridyl radicals can be present, for example, as pyridine N-oxides.

Halogen is fluorine, chlorine, bromine or iodine, preferably fluorine or chlorine.

Without restricting the present invention, examples of groups of compounds which can be used according to the invention are shown in the formulae Ia, Ib, Ic, Id, Ie, If, Ig and Ih, in which $A^2$ in the formula I has specific meanings. In the formulae Ia, Ib, Ic, Id, Ie, If, Ig and Ih, $A^1$, $R^2$ and $R^3$ have the meanings indicated above for the formula I, the number k in the formula Ib is 1, 2, 3, 4 or 5.

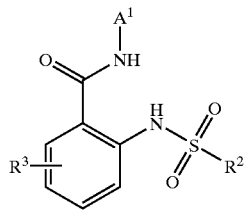

Ia

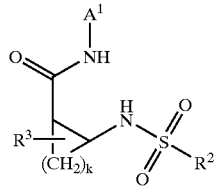

Ib

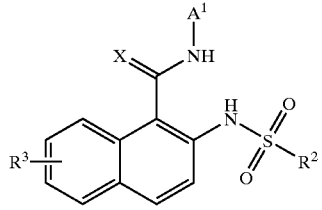

Ic

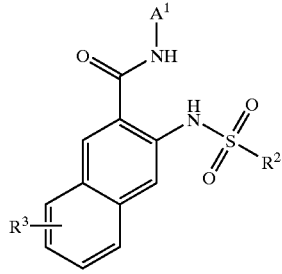

Id

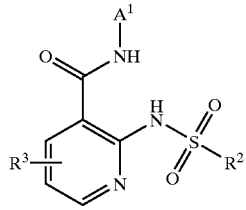

Ie

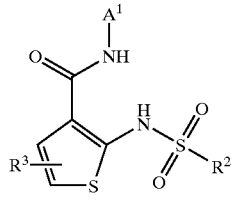

If

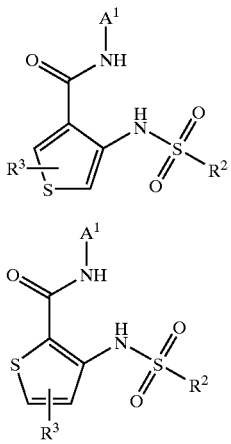

The present invention includes all stereoisomeric forms of the compounds of the formula I. Asymmetric centers contained in the compounds of the formula I can all independently of one another have the S configuration or the R configuration. The invention includes all possible enantiomers and diastereomers, as well as mixtures of two or more stereoisomeric forms, for example mixtures of enantiomers and/or diastereomers, in all ratios. Enantiomers are thus included by the invention in enantiomerically pure form, both as dextrorotatory and as levorotatory antipodes, in the form of racemates and in the form of mixtures of the two enantiomers in all ratios. In the presence of cis/trans isomerism the invention relates both to the cis form and the trans form and mixtures of these forms in all ratios. Individual stereoisomers can be prepared, if desired, by resolution of a mixture according to customary methods, for example by chromatography or crystallization, by use of stereochemically homogeneous starting substances in the synthesis or by stereoselective synthesis. If appropriate, derivatization can be carried out before separation of stereoisomers. The separation of a stereoisomer mixture can be carried out at the stage of the compounds of the formula I or at the stage of an intermediate in the course of the synthesis. If mobile hydrogen atoms are present, the present invention also includes all tautomeric forms of the compounds of the formula I.

If the compounds of the formula I contain one or more acidic or basic groups, the invention also relates to the corresponding physiologically or toxicologically tolerable salts, in particular the pharmaceutically utilizable salts. Thus the compounds of the formula I which contain acidic groups can be present in these groups, for example, as alkali metal salts, alkaline earth metal salts or as ammonium salts and can be used according to the invention. Examples of such salts are sodium salts, potassium salts, calcium salts, magnesium salts or salts with ammonia or organic amines such as, for example, ethylamine, ethanolamine, triethanolamine or amino acids. Compounds of the formula I which contain one or more basic, i.e. protonatable, groups can be present and can be used according to the invention in the form of their acid addition salts with physiologically tolerable inorganic or organic acids, for example as salts with hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid etc. If the compounds of the formula I simultaneously contain acidic and basic groups in the molecule, in addition to the salt forms outlined the invention also includes internal salts or betaines (zwitterions). Salts can be obtained from the compounds of the formula I by customary processes known to the person skilled in the art, for example by combination with an organic or inorganic acid or base in a solvent or dispersant, or alternatively from other salts by anion exchange or cation exchange.

The present invention furthermore includes all solvates of compounds of the formula I, for example hydrates or adducts with alcohols, and also derivatives of the compounds of the formula I such as, for example, esters, and prodrugs and active metabolites.

$A^1$ is preferably phenyl, naphthyl or bicyclic heteroaryl, which can all be substituted by one or more identical or different radicals $R^1$. Bicyclic heteroaryl representing $A^1$ is particularly preferably bicyclic heteroaryl having 10 ring members, which preferably contains one or two nitrogen atoms, in particular one nitrogen atom, as ring heteroatoms. Very particularly preferably, bicyclic heteroaryl representing $A^1$ is a radical derived from quinoline.

$A^2$, together with the two atoms carrying the group $R^2$—$SO_2$—NH and the group CO—NH, preferably forms an aromatic ring, particularly preferably a benzene ring or a thiophene ring.

$A^1$ can be unsubstituted, that is only carry hydrogen atoms, or can be substituted as indicated by one or more, for example one, two, three or four, identical or different radicals $R^1$. Preferably, a substituted radical $A^1$ is substituted by one, two or three, in particular one or two, radicals $R^1$. Radicals $R^1$ are preferably bonded to carbon atoms in $A^1$ which are not directly adjacent to the carbon atom which carries the group CO—NH. If $A^1$ is phenyl, radicals $R^1$ are particularly preferably in the meta-position and/or in the para-position, relative to the carbon atom which carries the group CO—NH. If a phenyl radical representing $A^1$ carries a radical $R^1$, this radical in many cases is particularly advantageously present in the para-position. If a phenyl radical representing $A^1$ carries a trifluoromethyl group as a radical $R^1$, this is preferably in the meta-position. If a phenyl radical representing $A^1$ carries two radicals $R^1$ representing chlorine, the two chlorine atoms are preferably in positions 3 and 4.

Preferred radicals $R^1$ are halogen, in particular chlorine, trifluoromethyl, $(C_3$–$C_7)$-alkyl, carboxymethyl, $CONR^5R^6$, 5-membered to 7-membered heterocyclyl, —O-aryl, —CO—$(C_1$–$C_{10})$-alkyl, —CO-aryl, —NH—CO—$(C_1$–$C_{10})$-alkyl, —NH—CO-aryl, —N(CO—$(C_1$–$C_{10})$-alkyl)$_2$, —N(CO-aryl)$_2$, —NH—$SO_2$—$(C_1$–$C_{10})$-alkyl, —NH—$SO_2$-aryl, —N($SO_2$-aryl)$_2$ and —N($SO_2$—$(C_1$–$C_{10})$-alkyl)$_2$, where all alkyl radicals can be substituted by one or more identical or different radicals $R^4$. In a group $CONR^5R^6$ representing $R^1$, $R^5$ and $R^6$, together with the nitrogen atom to which they are bonded, preferably form a 5-membered to 8-membered saturated or partially unsaturated ring, which in addition to the nitrogen atom carrying the groups $R^5$ and $R^6$ can also contain one or more further ring heteroatoms from the group consisting of N, O and S and which can be substituted as indicated above by one or more identical or different substituents. A group of particularly preferred radicals $R^1$ is formed by the radicals halogen, in particular chlorine, trifluoromethyl, —O-aryl, —NH—CO—$(C_1$–$C_{10})$-alkyl, —NH—CO-aryl, —NH—$SO_2$—$(C_1$–$C_{10})$-alkyl and —NH—$SO_2$-aryl, where all alkyl radicals can be substituted by one or more identical or different radicals $R^4$. A further group of particularly preferred radicals $R^1$ is formed by the radicals $CONR^5R^6$, —CO—$(C_1-C_{10})$-alkyl, —CO-aryl, —NH—CO—$(C_1-C_{10})$-alkyl, —NH—CO-aryl, —N(CO—$(C_1-C_{10})$-alkyl)$_2$, —N(CO-aryl)$_2$, —NH—SO$_2$—$(C_1-C_{10})$-alkyl, —NH—SO$_2$-aryl, —N(SO$_2$-aryl)$_2$ and —N(SO$_2$—$(C_1-C_{10})$-alkyl)$_2$, where all alkyl radicals can be substituted by one or more identical or different radicals $R^4$.

$R^2$ is preferably aryl, particularly preferably phenyl or 5-membered or 6-membered heteroaryl, where the radicals can be unsubstituted or substituted as indicated above. Very particularly preferably, $R^2$ is phenyl, thienyl or pyrazolyl, which can all in each case be substituted by one or two identical or different radicals from the group consisting of halogen, $CF_3$ and $(C_1-C_3)$-alkyl.

The rings representing $A^2$ can be unsubstituted, that is only carry $R^3$ representing hydrogen, or be substituted as indicated, that is carry one or more radicals $R^3$ other than hydrogen. The other substituent positions on the ring $A^2$, which do not carry any radical $R^3$ other than hydrogen, carry hydrogen atoms. If the ring $A^2$ carries one or more radicals $R^3$ which are other than hydrogen, it preferably carries one or two radicals $R^3$ of this type, in particular one radical $R^3$ of this type. Radicals $R^3$ of this type are preferably present in those positions of the ring $A^2$ which are not directly adjacent to the groups CO—NH and $R^2SO_2$—NH. If $A^2$ is a saturated or partially unsaturated carbocycle, $R^3$ of this type is preferably $(C_1-C_4)$-alkyl, in particular methyl. If $A^2$ is an aromatic ring, in particular if $A^2$ is a benzene ring, $R^3$ of this type is preferably $(C_1-C_3)$-alkyl, methoxy, halogen or $CF_3$, particularly preferably methyl or chlorine. If $A^2$ is an aromatic ring, in particular a benzene ring, it is very particularly preferred if this carries one chlorine atom as a substituent, that is if one radical $R^3$ representing chlorine is present and the other substituent positions on the benzene ring carry hydrogen atoms. If $A^2$ is a benzene ring, radicals $R^3$ other than hydrogen are preferably in positions 4 and/or 5. If only one radical $R^3$ of this type is present on a benzene ring representing $A^2$, this radical is preferably present in position 5 (relative to the group CO—NH in the 1-position).

If a group is substituted by one or more radicals $R^4$, it is preferably substituted by one, two or three, in particular one or two, identical or different radicals $R^4$. $R^4$ is preferably hydroxyl, $(C_1-C_4)$-alkyloxy, di-$((C_1-C_4)$-alkyl)amino or heteroaryl.

$R^5$ and $R^6$ are preferably independently of one another hydrogen, $(C_1-C_9)$-alkyl, —$(C_1-C_3)$-alkyl-O—$(C_1-C_4)$-alkyl or 5-membered or 6-membered aryl or, together with the nitrogen atom carrying $R^5$ and $R^6$, form a 5-membered to 7-membered heterocycle which additionally to the nitrogen atom carrying the groups $R^5$ and $R^6$ can also contain a further ring heteroatom from the group consisting of N, O and S and which can be substituted by one or more, for example one, two, three or four, identical or different radicals as indicated above, in particular by radicals from the group consisting of $(C_1-C_3)$-alkyl, 5-membered aryl and 6-membered aryl. Particularly preferably, $R^5$ and $R^6$, together with the nitrogen atom carrying them, form a 5-membered to 7-membered heterocycle which in addition to the nitrogen atom carrying the groups $R^5$ and $R^6$ can also contain a further ring heteroatom from the group consisting of N, O and S and which can be substituted by one or more, for example one, two, three or four, identical or different radicals as indicated above, in particular by radicals from the group consisting of $(C_1-C_3)$-alkyl, 5-membered aryl and 6-membered aryl. Very particularly preferably, such a ring, which is formed from $R^5$ and $R^6$ together with the nitrogen atom carrying them, is derived from morpholine, thiomorpholine, 1,1-dioxo-thiomorpholine, 1-oxothiomorpholine, 3,5-dimethylmorpholine, cis-3,5-dimethylmorpholine, 1-(pyrimidin-2-yl)piperazine, piperidin-4-carboxamide, 1-(2-hydroxyethyl)piperazine, 1-methylpiperazine, 1-ethylpiperazine, from 1-arylpiperazines, from ethyl piperazine-1-carboxylate, piperidine, 2-methylpiperidine, 4-hydroxypiperidine, from 4-oxopiperidine or a ketal thereof such as 1,4-dioxa-8-azaspiro[4.5]decane, from tetrahydropyridine, tetrahydropyrimidine, 1-methylhomopiperazine, thiazolidine, pyrroline, 3-hydroxypyrrolidine, 1,2,3,4-tetrahydroisoquinoline or 2,3-dihydro-1H-isoindole, where the ring is bonded via the ring nitrogen atom or, in the case of the piperazine derivatives, via the nonsubstituted ring nitrogen atom. Especially preferably, such a ring which is formed from $R^5$ and $R^6$ together with the nitrogen atom carrying them is derived from morpholine, thiomorpholine, 1,1-dioxothiomorpholine, 1-oxothiomorpholine, 3,5-dimethylmorpholline, cis-3,5-dimethylmorpholine, 1-(pyrimidin-2-yl)-piperazine, piperidine-4-carboxamide, 1,2,3,4-tetrahydroisoquinoline or 2,3-dihydro-1H-isoindole.

$R^8$ is preferably hydrogen, $(C_1-C_3)$-alkyl, di-$((C_1-C_4)$-alkyl)amino or —$(C_1-C_3)$-alkyl-O—$(C_1-C_4)$-alkyl.

$R^9$ is preferably hydrogen, $(C_1-C_3)$-alkyl or acetyl.

Aryl is preferably phenyl or heteroaryl, in particular phenyl or 5-membered or 6-membered heteroaryl. Preferred substituents in aryl radicals are halogen, $CF_3$, $(C_1-C_3)$-alkyl, cyano, nitro and $(C_1-C_3)$-alkyloxy, particularly preferred substituents are $CF_3$, chlorine, methyl and methoxy.

Heteroaryl preferably represents radicals which are derived from the heteroaromatics thiophene, pyrazole, thiazole, oxazole, pyridine, pyrimidine, pyridazine and tetrazole.

Heterocyclyl preferably represents radicals which are derived from saturated heterocycles, in particular radicals which are derived from pyrrolidine, piperidine, from N-alkylpiperazines, from morpholine, from dialkylmorpholines, from thiomorpholine or tetrahydrofuran.

If a group $S(O)_n$ is bonded to a nitrogen atom, the number n therein is preferably 1 or 2, particularly preferably 2.

Preferred compounds according to the present invention are compounds of the formula I in which one or more of-the radicals contained therein have preferred meanings, where all combinations of preferred substituent definitions are the subject of the present invention. Also, of all preferred compounds of the formula I, the present invention relates to all their stereoisomeric forms and mixtures thereof in all ratios, and their physiologically tolerable salts. A group of preferred compounds according to the present invention is formed, for example, from those compounds of the formula I in which $A^1$ is phenyl which carries a radical $R^1$ in the 4-position; the ring $A^2$ which includes the carbon atoms which carry the groups CO—NH— and NH—SO$_2R^2$ is a benzene ring or a thiophene ring; and $R^1$ is a substituent from the group consisting of CO—$(C_1-C_{10})$-alkyl, CO-aryl, CO—NR$^5$R$^6$, —NH—CO—$(C_1-C_{10})$-alkyl, —NH—CO-aryl, —N(CO—$(C_1-C_{10})$-alkyl)$_2$, —N(CO-aryl)$_2$, —NH—SO$_2$—$(C_1-C_{10})$-alkyl, —NH—SO$_2$-aryl, —N(SO$_2$—$(C_1-C_{10})$-alkyl)$_2$ and —N(SO$_2$-aryl)$_2$, in which all alkyl radicals can be substituted by one or more identical or different radicals $R^4$; in all their stereoisomeric forms and mixtures thereof in all ratios, and their physiologically tolerable salts.

Compounds of the formula I can be prepared according to or analogously to the processes described in the literature.

Reference is expressly made here to the corresponding contents of documents in which compounds of the formula I are already described, for example DE-A-35 23 705 and its equivalents. The respective contents of these documents is part of the present disclosure. The preparation of compounds of the formula I is moreover explained below.

According to scheme 1, an aminocarboxylic acid of the formula II can first be reacted with a sulfonyl chloride of the formula $R^2$—$SO_2$—Cl or a sulfonic anhydride in the presence of a base in a solvent such as water, pyridine or an ether.

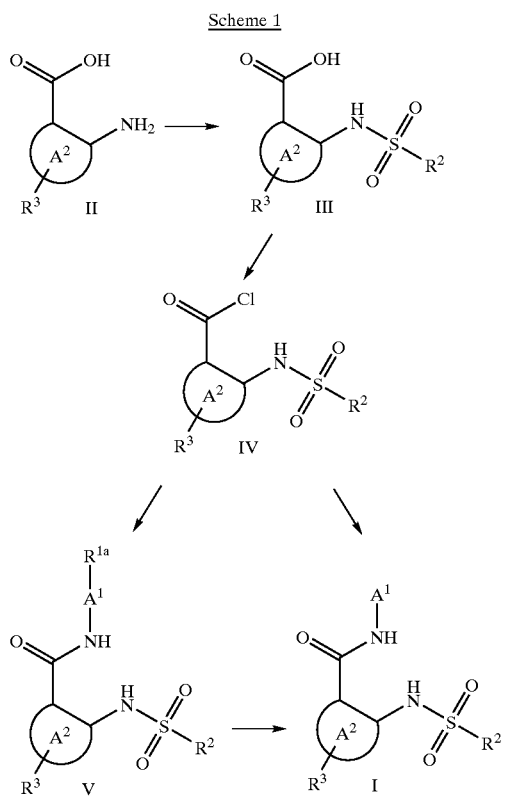

Scheme 1

Suitable bases are inorganic bases such as, for example, sodium carbonate or organic bases such as, for example, pyridine or triethylamine. The sulfonylaminocarboxylic acid of the formula III obtained can then be activated, for example, by reaction with a chlorinating agent such as, for example, phosphorus pentachloride, phosphorus oxychloride or thionyl chloride in an inert solvent to give an acid chloride of the formula IV and then reacted with an arylamine. The activation of the carboxylic acid group in the compound of the formula III, however, can also be carried out in another way, for example by one of the numerous methods familiar to the person skilled in the art, which are used in peptide chemistry for the linkage of amide bonds, for example by conversion into a mixed anhydride or an activated ester or using a carbodiimide such as dicyclohexylcarbodiimide.

The reaction of the activated sulfonylaminocarboxylic acid with an arylamine is advantageously carried out in an inert solvent such as, for example, pyridine, tetrahydrofuran or toluene with without without addition of an inert auxiliary base, for example of a tertiary amine or of pyridine. If the arylamine employed in the reaction with the activated carboxylic acid already contains the desired substituent(s) $R^1$ in the group $A^1$, i.e., if the arylamine has the formula $A^1$-$NH_2$ in which the group $A^1$ as indicated above can contain one or more substituents $R^1$, the reaction thus leads directly to the final product of the formula I. The activated carboxylic acids, however, can also first be reacted with an arylamine of the formula $R^{1a}$—$A^1$—$NH_2$, in which $R^{1a}$ is hydrogen or one or more of the groups $R^1$ which can be contained as substituents in $A^1$, or $R^{1a}$ is one or more groups which can be converted into groups $R^1$ according to the above definition. For example, $R^{1a}$ can be a hydrogen atom which is replaced in an electrophilic reaction by another radical such as, for example, a halogen atom or an aldehyde group, or an ester group which is converted into an amide group. The conversion of the reaction product of the formula V first obtained into a compound of the formula I can be carried out by standard processes.

Compounds of the formula I can also be obtained, for example, by first activating a suitably substituted nitrocarboxylic acid of the formula VI, for example by conversion into the corresponding acid chloride of the formula VII or in another way, and then reacted, for example, with a substituted arylamine of the formula $A^1$—$NH_2$ analogously to the processes described above (see Scheme 2).

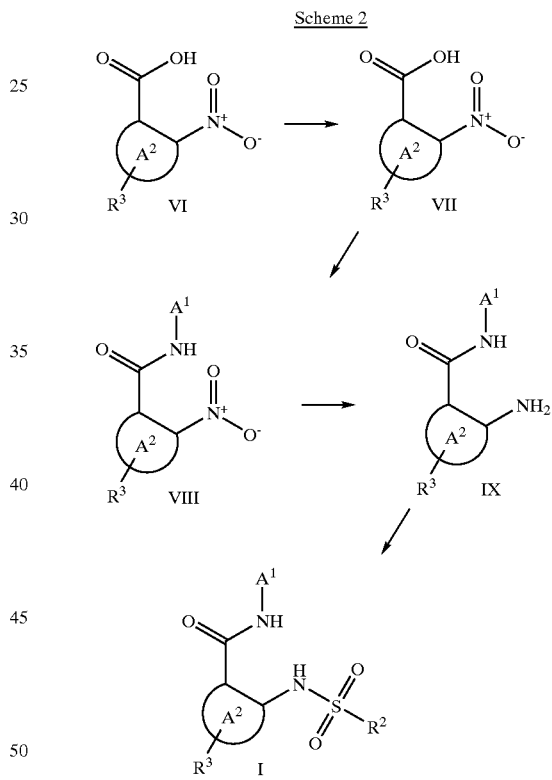

Scheme 2

Before the nitro group is reduced to the amino group in the nitro intermediate products of the formula VIII obtained, the activating action of the nitro group on the ring $A^2$ can be utilized and a suitable radical $R^3$, for example a halogen atom, can be replaced by another radical $R^3$ by reaction with a nucleophile, for example an amine. The reduction of the nitro group to the amino group can be carried out, for example, by catalytic hydrogenation in the presence of a noble metal catalyst or preferably in the presence of Raney nickel in a solvent such as ethanol, glacial acetic acid or ethanolic hydrochloric acid, or by reduction with a base metal such as tin, zinc or iron in the presence of acid. The reduction can also be carried out, for example, with tin(II) chloride or by reaction with sodium dithionite, advantageously, for example, in a mixture of methanol, tetrahydrofuran and water as the solvent. The sulfonylation of the amino group in the reduction product of the formula IX using an activated sulfonic acid derivative analogously to the reactions described above, for example using a sulfonyl chloride in the presence of pyridine, finally affords the compound of the formula I. Instead of an arylamine of the formula $A^1$—$NH_2$, an arylamine of the formula $R^{1a}$—$A^1$—$NH_2$ can also in turn be employed, in which $R^{1a}$ has the meaning indicated above, and the group or the groups $R^{1a}$ are then converted into the group or the groups $R^1$.

All reactions for the synthesis of the compounds of the formula I are well known per se to the person skilled in the art and can be carried out under standard conditions. Details to this end are found, for example, in Houben-Weyl, Methoden der Organischen Chemie [Methods of Organic Chemistry], Thieme-Verlag, Stuttgart, or Organic Reactions, John Wiley & Sons, New York. Depending on the conditions in the individual case, it can also be advantageous or necessary, in order to avoid side reactions in the synthesis of the compounds of the formula I, to temporarily block certain functional groups by the introduction of protective groups and later to liberate them again or first to employ functional groups in the form of precursors from which the desired functional group is then produced in a later step. Such synthesis strategies and the protective groups or precursors suitable for the individual case are known to the person skilled in the art. The compounds of the formula I obtained can optionally be purified by customary purification methods, for example by recrystallization or chromatography. Starting compounds for the preparation of the compounds of the formula I are commercially obtainable or can be prepared according to or analogously to literature procedures.

The compounds of the formula I bring about an increase in the cGMP concentration by means of the activation of soluble guanylate cyclase (sGC) and are therefore valuable agents for the therapy and prophylaxis of diseases which are associated with a low or reduced cGMP level or are caused by such a level or for whose therapy or prophylaxis an increase or normalization in the cGMP level present is desired. The activation of sGC by the compounds of the formula I can be investigated, for example, in the activity assay described below.

Diseases and pathological conditions which are associated with a low cGMP level or in which an increase or normalization in the cGMP level is desired and for whose therapy and prophylaxis compounds of the formula I can be employed are, for example, cardiovascular disorders such as endothelial dysfunction, diastolic dysfunction, atherosclerosis, high blood pressure, stable and unstable angina pectoris, thromboses, restenoses, myocardial infarct, strokes, cardiac insufficiency or pulmonary hypertension, or, for example, erectile dysfunction, bronchial asthma, chronic renal insufficiency and diabetes. Compounds of the formula I can moreover be employed in the therapy of liver cirrhosis and for improving restricted learning capacity or memory power. Preferably, the compounds of the formula I are employed in cardiovascular disorders such as endothelial dysfunction, diastolic dysfunction, atherosclerosis, high blood pressure, stable and unstable angina pectoris, thromboses, restenoses, myocardial infarct, strokes, cardiac insufficiency or pulmonary hypertension, in erectile dysfunction or for improving restricted learning capacity or memory power.

The compounds of the formula I and their physiologically tolerable salts can thus be used in animals, preferably in mammals, and in particular in man, as pharmaceuticals on their own, in mixtures with one another or together with other active compounds. The present invention therefore in particular also relates to the use of compounds of the formula I and their physiologically tolerable salts for the production of a medicament for the therapy or prophylaxis of the abovementioned syndromes, and the use for the production of a medicament for increasing or normalizing a disturbed cGMP balance. The invention likewise relates to the use of the compounds of the formula I and their physiologically tolerable salts for the activation of soluble guanylate cyclase, their use for the therapy or prophylaxis of the abovementioned syndromes and their use for increasing or normalizing a disturbed cGMP balance.

Pharmaceuticals according to the present invention can be administered orally, for example in the form of pills, tablets, film-coated tablets, coated tablets, granules, hard and soft gelatin capsules, aqueous, alcoholic or oily solutions, syrups, emulsions or suspensions, or rectally, for example in the form of suppositories. Administration, however, can also be carried out parenterally, for example subcutaneously, intramuscularly or intravenously in the form of injection solutions or infusion solutions. Further possible administration forms are, for example, percutaneous or topical application, for example in the form of ointments, tinctures, sprays or transdermal therapeutic systems, or administration by inhalation in the form of nasal sprays or aerosol mixtures, or, for example, microcapsules, implants or rods. The preferred administration form depends, for example, on the disease to be treated and its severity.

The medicaments according to the invention can be produced according to known standard processes for the production of pharmaceutical preparations. For this, one or more compounds of the formula I and/or their physiologically tolerable salts are brought, together with one or more solid or liquid pharmaceutical vehicles and/or additives or auxiliaries and, if desired, in combination with other pharmaceutical active compounds having therapeutic or prophylactic action, into a suitable administration form or dose form, which can then be used as a pharmaceutical in human or veterinary medicine. The pharmaceutical preparations contain a therapeutically or prophylactically active dose of the compounds of the formula I and/or their physiologically tolerable salts, which normally makes up 0.5 to 90% by weight of the pharmaceutical preparation.

For the production, for example, of pills, tablets, coated tablets and hard gelatin capsules, it is possible to use lactose, starch, for example corn starch, or starch derivatives, talc, stearic acid or its salts, etc. Vehicles for soft gelatin capsules and suppositories are, for example, fats, waxes, semisolid and liquid polyols, natural or hardened oils etc. Suitable vehicles for the preparation of solutions, for example injection solutions, or of emulsions or syrups are, for example, water, physiological saline solution, alcohols such as ethanol, glycerol, polyols, sucrose, invert sugar, glucose, mannitol, vegetable oils etc. The compounds of the formula I and their physiologically tolerable salts can also be lyophilized and the lyophilizates obtained used, for example, for the production of injection preparations or infusion preparations. Suitable vehicles for microcapsules, implants or rods are, for example, copolymers of glycolic acid and lactic acid.

In addition to the active compounds and vehicles, the pharmaceutical preparations can additionally contain customary additives, for example fillers, disintegrants, binders, lubricants, wetting agents, stabilizers, emulsifiers, dispersants, preservatives, sweetening agents, colorants, flavorings or aromatizers, thickening agents, diluents, buffer substances, furthermore solvents or solubilizers or agents for achieving a depot effect, salts for altering the osmotic pressure, coating agents or antioxidants.

The dose of the active compound of the formula I to be administered and/or of one of [lacuna] physiologically tolerable salts depends on the individual case and is to be suited to the individual conditions as customary for an optimal action. Thus it depends on the nature and severity of the disease to be treated, on the sex, age, weight and individual responsiveness of the human or animal to be treated, on the potency and duration of action of the compounds employed, on whether the therapy is acute or chronic or prophylaxis is carried out, or on whether further active compounds are administered in addition to compounds of the formula I. In general, a daily dose of approximately 0.01 to 100 mg/kg, preferably 0.1 to 10 mg/kg, in particular 0.3 to 5 mg/kg (in each case mg/kg of body weight) is appropriate in the case of administration to an adult of about 75 kg in weight to achieve the desired action. The daily dose can be administered in a single dose or, in particular in the case of administration of relatively large amounts, divided into a number of, for example two, three or four, individual doses. If appropriate, depending on individual behavior, it may be necessary to deviate upward or downward from the daily dose indicated. Pharmaceutical preparations normally contain 0.2 to 500 mg, preferably 1 to 200 mg, of active compound of the formula I and/or its physiologically tolerable salts.

The compounds of the formula I activate soluble guanylate cyclase, especially by binding in the heme binding pocket of the enzyme. On account of this property, apart from as pharmaceutical active compounds in human medicine and veterinary medicine, they can also be employed as a scientific tool or as an aid for biochemical investigations in which an effect on guanylate cyclase of this type is intended, and also for diagnostic purposes, for example in the in vitro diagnosis of cell or tissue samples. In addition, the compounds of the formula I and their salts, as already mentioned above, can serve as intermediates for the preparation of further pharmaceutical active compounds.

In addition to already known compounds, the formula I with the above general definition of the radicals also includes compounds which have not yet been described. The present invention also relates to the not yet known compounds of the formula I as such. The present invention thus also relates to compounds of the formula Ii

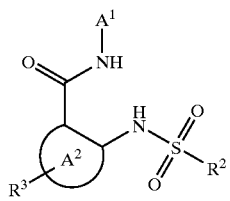

Ii in which

A$^1$ is a radical from the group consisting of phenyl, naphthyl and heteroaryl, which can all be substituted by one or more identical or different radicals R$^1$;

the ring A$^2$, which includes the carbon atoms which carry the groups CO—NH— and NH—SO$_2$R$^2$, is a benzene ring, a naphthalene ring, a saturated or partially unsaturated 3-membered to 7-membered carbocycle, a saturated, partially unsaturated or aromatic monocyclic 5-membered to 7-membered heterocycle which contains one or more ring heteroatoms from the group consisting of N, O and S, or a saturated, partially unsaturated or aromatic bicyclic 8-membered to 10-membered heterocycle which contains one or more ring heteroatoms from the group consisting of N, O and S;

R$^1$ is halogen, aryl, CF$_3$, NO$_2$, OH, —O—(C$_1$–C$_7$)-alkyl, —O—(C$_2$–C$_4$)-alkyl-O—(C$_1$–C$_7$)-alkyl, —O-aryl, (C$_1$–C$_2$)-alkylenedioxy, NR$^5$R$^6$, CN, CO—NR$^5$R$^6$, COOH, CO—O—(C$_1$–C$_5$)-alkyl, heterocyclyl, CHO, CO—(C$_1$–C$_{10}$)-alkyl, CO-aryl or (C$_1$–C$_{10}$)-alkyl which can be substituted by one or more identical or different radicals R$^4$;

R$^2$ is aryl, heterocyclyl, NR$^5$R$^6$;

R$^3$ is one or more identical or different substituents from the group consisting of halogen, CF$_3$, OH, —O—(C$_1$–C$_{10}$)-alkyl, —O—(C$_1$–C$_7$)-alkyl-R$^7$, —O-aryl, SH, —S—(C$_1$–C$_{10}$)-alkyl, —S—(C$_1$–C$_7$)-alkyl-R$^7$, —S-aryl, (C$_1$–C$_3$)-alkylenedioxy, CN, NO$_2$, NR$^8$R$^9$, CO—NR$^5$R$^6$, COOH, CO—O—(C$_1$–C$_5$)-alkyl, heterocyclyl, S(O)$_n$—(C$_1$–C$_7$)-alkyl, S(O)$_n$-aryl, S(O)$_n$—NR$^5$R$^6$ and (C$_1$–C$_7$)-alkyl which can be substituted by one or more identical or different radicals R$^4$;

R$^4$ is fluorine, OH, —O—(C$_1$–C$_{10}$)-alkyl, —O—(C$_1$–C$_7$)-alkyl-R$^7$, —O-aryl, SH, —S—(C$_1$–C$_{10}$)-alkyl, —S—(C$_1$–C$_7$)-alkyl-R$^7$, —S-aryl, —P(O)(O—(C$_1$–C$_5$)-alkyl)$_2$, —P(O)(OH)$_2$, CN, NR$^8$R$^9$, CO—NH$_2$, CO—NH—(C$_1$–C$_3$)-alkyl, CO—N((C$_1$–C$_3$)-alkyl)$_2$, COOH, CO—O—(C$_1$–C$_5$)-alkyl, heterocyclyl or oxo;

R$^5$ is hydrogen, (C$_1$–C$_{10}$)-alkyl which can be substituted by one or more identical or different substituents R$^4$ and/or by aryl, or is aryl, heterocyclyl, CO—(C$_1$–C$_{10}$)-alkyl, CO-aryl, CO-heterocyclyl, SO$_2$—(C$_1$–C$_{10}$)-alkyl, SO$_2$-aryl or SO$_2$-heterocyclyl;

R$^6$, independently of R$^5$, has one of the meanings indicated for R$^5$, or R$^5$ and R$^6$, together with the nitrogen atom to which they are bonded, form a 5-membered to 8-membered saturated or partially unsaturated ring which, in addition to the nitrogen atom carrying the groups R$^5$ and R$^6$, can also contain one or more further ring heteroatoms from the group consisting of N, O and S and which can be substituted by one or more identical or different substituents from the group consisting of fluorine, (C$_1$–C$_5$)-alkyl, (C$_1$–C$_3$)-hydroxyalkyl, —(C$_1$–C$_3$)-alkyl-O—(C$_1$–C$_4$)-alkyl, aryl, CF$_3$, OH, —O—(C$_1$–C$_7$)-alkyl, —O-aryl, —O—(C$_2$–C$_4$)-alkyl-O—(C$_1$–C$_7$)-alkyl, (C$_2$–C$_3$)-alkylenedioxy, NR$^8$, R$^9$, CN, CO-NH$_2$, CO—NH—(C$_1$–C$_3$)-alkyl, CO—N((C$_1$–C$_3$)-alkyl)$_2$, COOH, CO—O—(C$_1$–C$_5$)-alkyl, CHO, CO—(C$_1$–C$_5$)-alkyl, S(O)$_n$—(C$_1$–C$_4$)-alkyl, S(O)$_n$—NH$_2$, S(O)$_n$—NH—(C$_1$–C$_3$)-alkyl, S(O)$_n$—N((C$_1$–C$_3$)-alkyl)$_2$, oxo, —(CH$_2$)$_m$—NH$_2$, —(CH$_2$)$_m$—NH—(C$_1$–C$_4$)-alkyl and —(CH$_2$)$_m$—N((C$_1$–C$_4$)-alkyl)$_2$, where in the substituent —(CH$_2$)$_m$—N((C$_1$–C$_4$)-alkyl)$_2$ the two alkyl groups can be linked by a single bond and then together with the nitrogen atom carrying them form a 5-membered to 7-membered ring which in addition to the nitrogen atom and the carbon atoms can additionally also contain an oxygen atom, a sulfur atom or a group NR$^5$ as a ring member;

R$^7$ is OH, —O—(C$_1$–C$_7$)-alkyl, NH$_2$, —NH—(C$_1$–C$_4$)-alkyl or —N((C$_1$–C$_4$)-alkyl)$_2$, where in the substituent N((C$_1$–C$_4$)-alkyl)$_2$ the two alkyl groups can be linked by a single bond and then together with the nitrogen atom carrying them form a 5-membered to 7-membered ring which, in addition to the nitrogen atom and the carbon atoms, can additionally also contain an oxygen atom, a sulfur atom or a group $NR^5$ as a ring member;

$R^8$ is hydrogen or $(C_1-C_7)$-alkyl which can be substituted by one or more identical or different substituents from the group consisting of OH, —O—$(C_1-C_5)$-alkyl, $NH_2$, —NH—$(C_1-C_4)$-alkyl and —N$((C_1-C_4)$-alkyl$)_2$, where in the substituent N$((C_1-C_4)$-alkyl$)_2$ the two alkyl groups can be linked by a single bond and then, together with the nitrogen atom carrying them, form a 5-membered to 7-membered ring which, in addition to the nitrogen atom and the carbon atoms, can additionally also contain an oxygen atom, a sulfur atom or a group $NR^5$ as a ring member;

$R^9$, independently of $R^8$, has one of the meanings of $R^8$ or is CO—$(C_1-C_4)$-alkyl;

aryl is phenyl, naphthyl or heteroaryl, which can all be substituted by one or more identical or different substituents from the group consisting of halogen, $(C_1-C_5)$-alkyl, phenyl, tolyl, $CF_3$, $NO_2$, OH, —O—$(C_1-C_5)$-alkyl, —O—$(C_2-C_4)$-alkyl-O—$(C_1-C_3)$-alkyl, $(C_1-C_2)$-alkylenedioxy, $NH_2$, —NH—$(C_1-C_3)$-alkyl, —N$((C_1-C_3)$-alkyl$)_2$, NH—CHO, —NH—CO—$(C_1-C_5)$-alkyl, CN, CO—$NH_2$, CO—NH—$(C_1-C_3)$-alkyl, CO—N$((C_1-C_3)$-alkyl$)_2$, COOH, CO—O—$(C_1-C_5)$-alkyl, heterocyclyl, CHO, CO—$(C_1-C_5)$-alkyl, S(O)$_n$—$(C_1-C_4)$-alkyl, S(O)$_n$-phenyl, S(O)$_n$-tolyl, S(O)$_2$—$NH_2$, S(O)$_2$—NH—$(C_1-C_3)$-alkyl and S(O)$_2$—N$((C_1-C_3)$-alkyl$)_2$;

heteroaryl is the radical of a monocyclic 5-membered or 6-membered aromatic heterocycle or a bicyclic 8-membered to 10-membered aromatic heterocycle, which in each case contain one or more ring heteroatoms from the group consisting of N, O and S;

heterocyclyl is the radical of a monocyclic or polycyclic, 5-membered to 11-membered saturated or partially unsaturated heterocycle, which contains one or more ring heteroatoms from the group consisting of N, O and S and which can be substituted by one or more identical or different substituents from the group consisting of fluorine, $(C_1-C_5)$-alkyl, OH, —O—$(C_1-C_5)$-alkyl, —O—$(C_2-C_4)$-alkyl-O—$(C_1-C_3)$-alkyl, $NH_2$, —NH—$(C_1-C_3)$-alkyl, —N$((C_1-C_3)$-alkyl$)_2$, CN, CO—$NH_2$, CO—NH—$(C_1-C_3)$-alkyl, CO—N$((C_1-C_3)$-alkyl$)_2$, COOH and CO—O—$(C_1-C_5)$-alkyl;

n is 0, 1 or 2;

m is 2, 3 or 4;

in all their stereoisomeric forms and mixtures thereof in all ratios, and their physiologically tolerable salts, where compounds of the formula Ii are excluded a) in which simultaneously $A^1$ is phenyl, $A^2$ together with the carbon atoms carrying the groups CO—NH and $R^2SO_2$—NH forms a benzene ring and $R^1$ is radicals from the group consisting of halogen, phenyloxy, naphthyloxy, 1,3-benzothiazol-2-yloxy, pyrimidin-4-yloxy and pyrimidin-6-yloxy, which can all be unsubstituted or substituted;

b) or in which $A^1$ or $R^2$ is 2,1,3-benzothiadiazol-4-yl;

c) or in which $A^1$ is 2-hydroxyphenyl, 2-ethoxycarbonylmethoxyphenyl, 2-carboxyphenyl, 2-carboxyalkylphenyl or 2-carbamoylphenyl;

d) or in which simultaneously the ring $R^3$-$A^2$, together with the carbon atoms carrying the groups CO—NH and $R^2SO_2$—NH, forms a benzene ring which is substituted in the 5-position by nitro or bromine or chlorine or is substituted in positions 5 and 6 by two chlorine atoms, $R^2$ is 4-chlorophenyl and $A^1$ is 3-trifluoromethylphenyl;

e) or in which the ring $R^3$-$A^2$, together with the carbon atoms carrying the groups CO—NH and $R^2SO_2$—NH, forms an indole ring on which the sulfonylamino group is in the 2-position, a 5-aminopyrazole ring on which the sulfonylamino group is in the 3-position, a 4-hydroxyquinoline ring on which the sulfonylamino group is in the 2-position, a pyrazolo[1,5-a]pyrimidine ring on which the sulfonylamino group is in the 2-position, or a cyclohexane ring;

f) or in which simultaneously the ring $R^3$-$A^2$ together with the carbon atoms carrying the groups CO—NH and $R^2SO_2$—NH forms a benzene ring, $R^2$ is 4-tolyl and $A^1$ is 4-pyridyl.

All explanations which were given for the compounds of the formula I with the associated definition of the substituents given at the outset apply correspondingly to the compounds of the formula Ii with the above definition of the substituents. This is applicable, for example, to the fact that groups and substituents which occur a number of times are all independent of one another, or to all explanations for alkyl groups, aryl groups, heterocyclic radicals, possible substituents, salts, isomers, tautomers, etc. The present invention also includes all salts of the compounds of the formula Ii, which because of low physiological tolerability are not directly suitable for use in pharmaceuticals, but, for example, are suitable as intermediates for chemical syntheses or for the preparation of physiologically tolerable salts. As in the compounds of the formula I, the ring $A^2$ in the compounds of the formula Ii can also have, for example, the meanings shown in the formulae Ia, Ib, Ic, Id, Ie, If, Ig and Ih, if these are not excluded in the definition of the substituents in the formula Ii.

All preferred meanings of the radicals in the formula I also apply correspondingly to the radicals in the formula Ii. Likewise, preferred compounds of the formula Ii are those compounds in which one or more of the radicals have preferred meanings, where all combinations of preferred substituent definitions are a subject of the present invention. A group of preferred compounds of the formula Ii is formed, for example, of those compounds in which $A^1$ is phenyl which carries a radical $R^1$ in the 4-position; the ring $A^2$, which includes the carbon atoms which carry the groups CO—NH— and NH—$SO_2R^2$, is a benzene ring or a thiophene ring; and $R^1$ is a substituent from the group consisting of CO—$(C_1-C_{10})$-alkyl, CO-aryl, CO—$NR^5R^6$, —NH—CO—$(C_1-C_{10})$-alkyl, —NH—CO-aryl, —N(CO—$(C_1-C_{10})$-alkyl$)_2$, —N(CO-aryl)$_2$, —NH—$SO_2$—$(C_1-C_{10})$-alkyl, —NH—$SO_2$-aryl, —N($SO_2$—$(C_1-C_{10})$-alkyl$)_2$ and —N($SO_2$-aryl)$_2$, in which all alkyl radicals can be substituted by one or more identical or different radicals $R^4$; in all their stereoisomeric forms and mixtures thereof in all ratios, and their physiologically tolerable salts.

Furthermore, the present invention also relates to specific compounds of the formula I as such, in which the ring $A^2$, which includes the carbon atoms which carry the groups CO—NH— and NH—$SO_2R$, carries no further substituents, that is compounds of the formula I in which $R^3$ is hydrogen. In these compounds, $A^1$, $A^2$ and $R^1$ preferably have the meanings which are indicated above for the preferred compounds of the formula Ii. The present invention thus also relates to the compounds of the formula Ik,

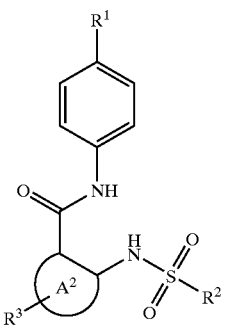

in which
the ring $A^2$, which includes the carbon atoms which carry the groups CO—NH— and NH—SO$_2$R$^2$, is a benzene ring or a thiophene ring;

R$^1$ is a substituent from the group consisting of CO—(C$_1$–C$_{10}$)-alkyl, CO-aryl, CO—NR$^5$R$^6$, —NH—CO—(C$_1$–C$_{10}$)-alkyl, —NH—CO-aryl, —N(CO—(C$_1$–C$_{10}$)-alkyl)$_2$, —N(CO-aryl)$_2$, —NH—SO$_2$—(C$_1$–C$_{10}$)-alkyl, —NH—SO$_2$-aryl, —N(SO$_2$—(C$_1$–C$_{10}$)-alkyl)$_2$ and —N(SO$_2$-aryl)$_2$, in which all alkyl radicals can be substituted by one or more identical or different radicals R$^4$;

R$^2$ is aryl, heterocyclyl or NR$^5$R$^6$;

R$^3$ is one or more identical or different substituents from the group consisting of hydrogen, halogen, CF$_3$, OH, —O—(C$_1$–C$_7$)-alkyl-R$^7$, —O-aryl, SH, —S—(C$_1$–C$_{10}$)-alkyl, —S—(C$_1$–C$_7$)-alkyl-R$^7$, —S-aryl, (C$_1$–C$_2$)-alkylenedioxy, CN, NO$_2$, NR$^8$R$^9$, CO—NR$^5$R$^6$, COOH, CO—O—(C$_1$–C$_5$)-alkyl, heterocyclyl, S(O)$_n$—(C$_1$–C$_7$)-alkyl, S(O)$_n$-aryl, S(O)$_n$—NR$^5$R$^6$ and (C$_1$–C$_7$)-alkyl which can be substituted by one or more identical or different radicals R$^4$;

R$^4$ is fluorine, OH, —O—(C$_1$–C$_{10}$)-alkyl, —O—(C$_1$–C$_7$)-alkyl-R$^7$, —O-aryl, SH, —S—(C$_1$–C$_{10}$)-alkyl, —S—(C$_1$–C$_7$)-alkyl-R$^7$, —S-aryl, —P(O)(O—(C$_1$–C$_5$)-alkyl)$_2$, —P(O)(OH)$_2$, CN, NR$^8$R$^9$, CO—NH$_2$, CO—NH—(C$_1$–C$_3$)-alkyl, CO—N((C$_1$–C$_3$)-alkyl)$_2$, COOH, CO—O—(C$_1$–C$_5$)-alkyl, heterocyclyl or oxo;

R$^5$ is hydrogen, (C$_1$–C$_{10}$)-alkyl which can be substituted by one or more identical or different substituents R$^4$ and/or by aryl, or is aryl, heterocyclyl, CO—(C$_1$–C$_{10}$)-alkyl, CO-aryl, CO-heterocyclyl, SO$_2$—(C$_1$–C$_{10}$)-alkyl, SO$_2$-aryl or SO$_2$-heterocyclyl;

R$^6$, independently of R$^5$, has one of the meanings indicated for R$^5$, or R$^5$ and R$^6$, together with the nitrogen atom to which they are bonded, form a 5-membered to 8-membered saturated or partially unsaturated ring, which in addition to the nitrogen atom carrying the groups R$^5$ and R$^6$ can also contain one or more further ring heteroatoms from the group consisting of N, O and S and which can be substituted by one or more identical or different substituents from the group consisting of fluorine, (C$_1$–C$_5$)-alkyl, (C$_1$–C$_3$)-hydroxyalkyl, —(C$_1$–C$_3$)-alkyl-O—(C$_1$–C$_4$)-alkyl, aryl, CF$_3$, OH, —O—(C$_1$–C$_7$)-alkyl, —O-aryl, —O—(C$_2$–C$_4$)-alkyl-O—(C$_1$–C$_7$)-alkyl, (C$_2$–C$_3$)-alkylenedioxy, NR$^8$R$^9$, CN, CO—NH$_2$, CO—NH—(C$_1$–C$_3$)-alkyl, CO—N((C$_1$–C$_3$)-alkyl)$_2$, COOH, CO—O—(C$_1$–C$_5$)-alkyl, CHO, CO—(C$_1$–C$_5$)-alkyl, S(O)$_n$—(C$_1$–C$_4$)-alkyl, S(O)$_n$—NH$_2$, S(O)$_n$—NH—(C$_1$–C$_3$)-alkyl, S(O)$_n$—N((C$_1$–C$_3$)-alkyl)$_2$, oxo, —(CH$_2$)$_m$—NH$_2$, —(CH$_2$)$_m$—NH—(C$_1$–C$_4$)-alkyl and —(CH$_2$)$_m$—N((C$_1$–C$_4$)-alkyl)$_2$, where in the substituent —(CH$_2$)$_m$—N((C$_1$–C$_4$)-alkyl)$_2$ the two alkyl groups can be linked by a single bond and then together with the nitrogen atom carrying them form a 5-membered to 7-membered ring which in addition to the nitrogen atom and the carbon atoms can additionally also contain an oxygen atom, a sulfur atom or a group NR$^5$ as a ring member;

R$^7$ is OH, —O—(C$_1$–C$_7$)-alkyl, NH$_2$, —NH—(C$_1$–C$_4$)-alkyl or —N((C$_1$–C$_4$)-alkyl)$_2$, where in the substituent N((C$_1$–C$_4$)-alkyl)$_2$ the two alkyl groups can be linked by a single bond and then together with the nitrogen atom carrying them form a 5-membered to 7-membered ring which in addition to the nitrogen atom and the carbon atoms can additionally also contain an oxygen atom, a sulfur atom or a group NR$^5$ as a ring member;

R$^8$ is hydrogen or (C$_1$–C$_7$)-alkyl which can be substituted by one or more identical or different substituents from the group consisting of OH, —O—(C$_1$–C$_5$)-alkyl, NH$_2$, —NH—(C$_1$–C$_4$)-alkyl and —N((C$_1$–C$_4$)-alkyl)$_2$, where in the substituent N((C$_1$–C$_4$)-alkyl)$_2$ the two alkyl groups can be linked by a single bond and then together with the nitrogen atom carrying them form a 5-membered to 7-membered ring which in addition to the nitrogen atom and the carbon atoms can additionally also contain an oxygen atom, a sulfur atom or a group NR$^5$ as a ring member;

R$^9$, independently of R$^8$, has one of the meanings of R$^8$ or is CO—(C$_1$–C$_4$)-alkyl;

aryl is phenyl, naphthyl or heteroaryl, which can all be substituted by one or more identical or different substituents from the group consisting of halogen, (C$_1$–C$_5$)-alkyl, phenyl, tolyl, CF$_3$, NO$_2$, OH, —O—(C$_1$–C$_5$)-alkyl, —O—(C$_2$–C$_4$)-alkyl-O—(C$_1$–C$_3$)-alkyl, (C$_1$–C$_2$)-alkylenedioxy, NH$_2$, —NH—(C$_1$–C$_3$)-alkyl, —N((C$_1$–C$_3$)-alkyl)$_2$, NH—CHO, —NH—CO—(C$_1$–C$_5$)-alkyl, CN, CO—NH$_2$, CO—NH—(C$_1$–C$_3$)-alkyl, CO—N((C$_1$–C$_3$)-alkyl)$_2$, COOH, CO—O—(C$_1$–C$_5$)-alkyl, heterocyclyl, CHO, CO—(C$_1$–C$_5$)-alkyl, S(O)$_n$—(C$_1$–C$_4$)-alkyl, S(O)$_n$-phenyl, S(O)$_n$-tolyl, S(O)$_2$—NH$_2$, S(O)$_2$—NH—(C$_1$–C$_3$)-alkyl and S(O)$_2$—N((C$_1$–C$_3$)-alkyl)$_2$;

heteroaryl is the radical of a monocyclic 5-membered or 6-membered aromatic heterocycle or of a bicyclic 8-membered to 10-membered aromatic heterocycle which in each case contain one or more ring heteroatoms from the group consisting of N, O and S;

heterocyclyl is the radical of a monocyclic or polycyclic, 5-membered to 11-membered saturated or partially unsaturated heterocycle which contains one or more ring heteroatoms from the group consisting of N, O and S and which can be substituted by one or more identical or different substituents from the group consisting of fluorine, (C$_1$–C$_5$)-alkyl, OH, —O—(C$_1$–C$_5$)-alkyl, —O—(C$_2$–C$_4$)-alkyl-O—(C$_1$–C$_3$)-alkyl, NH$_2$, —NH—(C$_1$–C$_3$)-alkyl, —N((C$_1$–C$_3$)-alkyl)$_2$, CN, CO—NH$_2$, CO—NH—(C$_1$–C$_3$)-alkyl, CO—N((C$_1$–C$_3$)-alkyl)$_2$, COOH and CO—O—(C$_1$–C$_5$)-alkyl;

n is 0, 1 or 2;

m is 2, 3 or 4;

in all their stereoisomeric forms and mixtures thereof in all ratios, and their physiologically tolerable salts.

All explanations which were given for the compounds of the formula I having the associated definition of the substituents given at the outset also apply, if applicable, correspondingly to the compounds of the formula Ik having the above definition of the substituents. This applies, for example, to the fact that groups and substituents which occur a number of times are all independent of one another, or to all explanations for alkyl groups, aryl groups, heterocyclic radicals, possible substituents, salts, isomers, tautomers, etc. The present invention also includes all salts of the compounds of the formula Ik which, because of low physiological tolerability, are not directly suitable for use in pharmaceuticals, but are suitable, for example, as intermediates for chemical syntheses or for the production of physiologically tolerable salts. As in the compounds of the formula I, the ring $A^2$ in the compounds of the formula Ik can also, for example, have the meanings shown in the formulae Ia, If, Ig and Ih. All preferred meanings of the radicals in the formula I also apply correspondingly to the radicals in the formula Ik. Likewise, preferred compounds of the formula Ik are those compounds in which one or more of the radicals have preferred meanings, where all combinations of preferred substituent definitions are a subject of the present invention.

Furthermore, the above details for the preparation of the compounds of the formula I and for their biological properties and for their use, and for pharmaceutical preparations comprising them naturally also apply to the compounds of the formulae Ii and Ik. The present invention also relates to processes for the preparation of the compounds of the formulae Ii and Ik defined above by the synthesis process described above, the compounds of the formulae Ii and Ik and their physiologically tolerable salts for use as pharmaceuticals and pharmaceutical preparations which contain an efficacious dose of at least one compound of the formulae Ii or Ik or of a physiologically tolerable salt thereof as active constituent in addition to customary pharmaceutically acceptable vehicles and/or additives.

The following example compounds, which were prepared according to or analogously to processes described in the literature, illustrate the invention without restricting it.

EXAMPLES 1) 2-(4-Chlorophenylsulfonylamino)-N-(3-trifluoromethylphenyl)benzamide M.p.: 169° C.
2) 5-Bromo-2-(4-chlorophenylsulfonylamino)-N-(3-trifluoromethylphenyl)benzamide M.p.: 220° C.
3) 2-(4-Chlorophenylsulfonylamino)-N-(2-naphthyl)benzamide M.p.: 189° C.
4) 5-Chloro-2-(4-chlorophenylsulfonylamino)-N-(3-trifluoromethylphenyl)benzamide M.p.: 216° C.
5) 5-Chloro-2-(4-chlorophenylsulfonylamino)-N-(4-phenoxyphenyl)benzamide M.p.: 205° C.
6) 5-Chloro-2-(4-chlorophenylsulfonylamino)-N-(4-(4-chlorophenoxy)-phenyl)benzamide M.p.: 207° C.
7) 2-(4-Chlorophenylsulfonylamino)-N-(4-phenoxyphenyl)benzamide M.p.: 143° C.
8) 5-Chloro-2-(4-chlorophenylsulfonylamino)-N-(3,4-dichlorophenyl)benzamide M.p.: 244° C.
9) 5-Chloro-2-(4-chlorophenylsulfonylamino)-N-(4-bromophenyl)benzamide M.p.: 210° C.
10) 5-Chloro-2-(4-chlorophenylsulfonylamino)-N-(3-chlorophenyl)benzamide M.p.: 228° C.
11) 5-Chloro-2-(4-chlorophenylsulfonylamino)-N-(4-methoxyphenyl)benzamide M.p.: 190° C.
12) 5-Chloro-2-(4-chlorophenylsulfonylamino)-N-(2-naphthyl)benzamide M.p.: 211° C.
13) 5-Chloro-2-(4-fluorophenylsulfonylamino)-N-(3,5-dichlorophenyl)benzamide M.p.: 250° C.
14) Ethyl 4-(5-chloro-2-(4-chlorophenylsulfonylamino)benzoylamino)benzoate M.p.: 185°
15) 5-Chloro-2-(4-chlorophenylsulfonylamino)-N-(4-(bismethylsulfonylamino)phenyl)benzamide M.p.: 235° C.
16) 5-Chloro-2-(4-chlorophenylsulfonylamino)-N-(4-isopropylphenyl)benzamide M.p.: 188° C.
17) 5-Chloro-2-(3-chloro-4-methoxyphenylsulfonylamino)-N-(4-fluorophenyl)benzamide M.p.: 188° C.
18) Ethyl 2-chloro-5-(5-chloro-2-(3,4-dichlorophenylsulfonylamino)benzoylamino)benzoate M.p.: 202° C.
19) 5-Chloro-2-(4-chlorophenylsulfonylamino)-N-(3-chloro-4-(4-chloronaphthalene-1-yloxy)phenyl)benzamide
20) 2-(4-Chlorophenylsulfonylamino)-5-chloro-N-(4-tert-butylphenyl)benzamide M.p.: 91° C.
21) 5-Chloro-2-(4-chlorophenylsulfonylamino)-N-(4-(morpholin-4-yl)phenyl)benzamide M.p.: 228.5° C.
22) 5-Chloro-2-(4-chlorophenylsulfonylamino)-N-(4-(phenylamino)-phenyl)benzamide M.p.: 192.5° C.
23) 5-Chloro-2-(4-chlorophenylsulfonylamino)-N-(4-(benzyloxy)phenyl)benzamide M.p.: 191° C.
24) 5-Chloro-2-(4-chlorophenylsulfonylamino)-N-(4-acetylphenyl)benzamide M.p.: 226° C.
25) 2-Phenylsulfonylamino-5-chloro-N-(4-(2-oxopyrrolidin-1-yl)phenyl)benzamide M.p.: 218° C.
26) 5-Chloro-2-(4-chlorophenylsulfonylamino)-N-(5-methylpyrazin-3-yl)benzamide M.p.: 248° C.
27) 5-Chloro-2-(4-chlorophenylsulfonylamino)-N-(3-(2-thienyl)pyrazol-5-yl)benzamide M.p.: 117° C.
28) 5-Chloro-2-(4-chlorophenylsulfonylamino)-N-(3,5-bis-trifluoromethylphenyl)benzamide M.p.: 182.5° C.
29) 5-Chloro-2-(4-chlorophenylsulfonylamino)-N-(2-methoxy-5-trifluoromethylphenyl)benzamide M.p.: 164.5° C.
30) 5-Chloro-2-(4-chlorophenylsulfonylamino)-N-(2-trifluoromethylphenyl)benzamide M.p.: 182° C.
31) 5-Chloro-2-(4-chlorophenylsulfonylamino)-N-(3-methoxyphenyl)benzamide M.p.: 163.5° C.
32) 5-Chloro-2-(4-chlorophenylsulfonylamino)-N-(3,5-dimethoxyphenyl)benzamide M.p.: 74.5° C.
33) 5-Chloro-2-(4-chlorophenylsulfonylamino)-N-(4-(morpholine-4-carbonyl)phenyl)benzamide
34) 5-Chloro-2-(4-chlorophenylsulfonylamino)-N-(4-(2,5-dioxopyrrolidin-1-yl)phenyl)benzamide
35) 5-Chloro-2-(4-chlorophenylsulfonylamino)-N-(1H-indol-5-yl)benzamide
36) 5-Chloro-2-(4-chlorophenylsulfonylamino)-N-(quinolin-8-yl)benzamide
37) 5-Chloro-2-(4-chlorophenylsulfonylamino)-N-(4-methyl-2-oxo-2H-chromen-7-yl)benzamide
38) 5-Chloro-2-(4-chlorophenylsulfonylamino)-N-(isoquinolin-5-yl)benzamide
39) 5-Chloro-2-(4-chlorophenylsulfonylamino)-N-(4-ethoxy-2-nitrophenyl)benzamide
40) 5-Chloro-2-(4-chlorophenylsulfonylamino)-N-(2-methoxy-5-nitrophenyl)benzamide
41) 5-Chloro-2-(4-chlorophenylsulfonylamino)-N-(2,5-dimethoxy-4-nitrophenyl)benzamide
42) 5-Chloro-2-(4-chlorophenylsulfonylamino)-N-(2-methoxy-4-nitrophenyl)benzamide
43) 5-Chloro-2-(4-chlorophenylsulfonylamino)-N-(2-cyanophenyl)benzamide
44) 5-Chloro-2-(4-chlorophenylsulfonylamino)-N-(4-cyano-2,3,5,6-tetrafluorophenyl)benzamide
45) 5-Chloro-2-(4-chlorophenylsulfonylamino)-N-(2-(2-hydroxyethyl)-phenyl)benzamide
46) 5-Chloro-2-(4-chlorophenylsulfonylamino)-N-(3-cyanophenyl)benzamide 47) 5-Chloro-2-(4-chlorophenylsulfonylamino)-N-(4-benzoylamino-5-chloro-2-methylphenyl)benzamide
48) 5-Chloro-2-(4-chlorophenylsulfonylamino)-N-(3-(1-hydroxyethyl)-phenyl)benzamide
49) 5-Chloro-2-(4-chlorophenylsulfonylamino)-N-(4-cyanophenyl)benzamide
50) N-(2-Benzoyl4-chlorophenyl)-5-chloro-2-(4-chlorophenylsulfonylamino)benzamide
51) 5-Chloro-2-(4-chlorophenylsulfonylamino)-N-(4-diethylaminophenyl)benzamide
52) N-(4-Butoxyphenyl)-5-chloro-2-(4-chlorophenylsulfonylamino)benzamide
53) 5-Chloro-2-(4-chlorophenylsulfonylamino)-N-(4-hexyloxyphenyl)benzamide
54) Diethyl (4-(5-chloro-2-(4-chlorophenylsulfonylamino)benzoylamino)benzyl)phosphonate
55) 5-Chloro-2-(4-chlorophenylsulfonylamino)-N-(4-pentylphenyl)benzamide
56) 5-Chloro-2-(4-chlorophenylsulfonylamino)-N-(3,4,5-trimethoxyphenyl)benzamide
57) Diethyl 2-(4-(5-chloro-2-(4-chlorophenylsulfonylamino)benzoylamino)benzoylamino)pentanedioate
58) 5-Chloro-2-(4-chlorophenylsulfonylamino)-N-(2-methoxydibenzofuran-3-yl)benzamide
59) Butyl 4-(5-chloro-2-(4-chlorophenylsulfonylamino)benzoylamino)benzoate
60) 5-Chloro-2-(4-chlorophenylsulfonylamino)-N-(2-phenoxyphenyl)benzamide
61) 5-Chloro-2-(4-chlorophenylsulfonylamino)-N-(3-phenoxyphenyl)benzamide
62) 5-Chloro-2-(4-chlorophenylsulfonylamino)-N-(4-hydroxybiphenyl-3-yl)benzamide
63) 5-Chloro-2-(4-chlorophenylsulfonylamino)-N-(4-hydroxy-2-nitrophenyl)benzamide
64) 5-Chloro-2-(4-chlorophenylsulfonylamino)-N-(3-hydroxymethyl-2-methylphenyl)benzamide
65) 5-Chloro-2-(4-chlorophenylsulfonylamino)-N-(5-hydroxymethyl-2-methylphenyl)benzamide
66) 5-Chloro-2-(4-chlorophenylsulfonylamino)-N-(4-(4-methylphenylsulfonylamino)phenyl)benzamide
67) 2-(5-Chloro-2-(4-chlorophenylsulfonylamino)benzoylamino)benzoic acid
68) tert-Butyl (4-(5-chloro-2-(4-chlorophenylsulfonylamino)benzoylamino)phenyl)carbamate
69) 5-Chloro-2-(4-chlorophenylsulfonylamino)-N-(3,4,5-trifluorophenyl)benzamide
70) 5-Chloro-2-(4-chlorophenylsulfonylamino)-N-(4-methyl-2-oxo-1,2-dihydroquinolin-7-yl)benzamide
71) 3-(5-Chloro-2-(4-chlorophenylsulfonylamino)benzoylamino)benzoic acid
72) 2-Diethylaminoethyl 4-(5-chloro-2-(4-chlorophenylsulfonylamino)benzoylamino)benzoate
73) 5-Chloro-2-(4-chlorophenylsulfonylamino)-N-(2-oxo-4-trifluoromethyl-2H-chromen-7-yl)benzamide
74) 5-Chloro-2-(4-chlorophenylsulfonylamino)-N-(2-hydroxymethyl-4-methylphenyl)benzamide
75) 5-Chloro-2-(4-chlorophenylsulfonylamino)-N-(2-(pyrrol-1-yl)phenyl)benzamide
76) 5-Chloro-2-(4-chlorophenylsulfonylamino)-N-(2-methyl-1,3-dioxo-2,3-dihydro-1H-isoindol-5-yl)benzamide
77) Ethyl 3-(5-chloro-2-(4-chlorophenylsulfonylamino)benzoylamino)benzoate
78) N-(Benzo[1,3]dioxol-5-yl)-5-chloro-2-(4-chlorophenylsulfonylamino)benzamide
79) 5-Chloro-2-(4-chlorophenylsulfonylamino)-N-(3-chloro-4-cyanophenyl)benzamide
80) Methyl 2-(5-chloro-2-(4-chlorophenylsulfonylamino)benzoylamino)-4,5-dimethoxybenzoate
81) 5-Chloro-2-(4-chlorophenylsulfonylamino)-N-(3-nitrophenyl)benzamide
82) Methyl 3-(5-chloro-2-(4-chlorophenylsulfonylamino)benzoylamino)benzoate
83) 5-Chloro-2-(4-chlorophenylsulfonylamino)-N-(2-(morpholin4-yl)-5-trifluoromethylphenyl)benzamide
84) N-(1H-Benzotriazol-5-yl)-5-chloro-2-(4-chlorophenylsulfonylamino)benzamide
85) 5-Chloro-2-(4-chlorophenylsulfonylamino)-N-(4-methoxymethyl-2-oxo-2H-chromen-7-yl)benzamide
86) N-(2-(1H-Benzimidazol-2-yl)phenyl)-5-chloro-2-(4-chlorophenylsulfonylamino)benzamide
87) 5-Chloro-2-(4-chlorophenylsulfonylamino)-N-(2-(N-phenylcarbamoyl)phenyl)benzamide
88) N-(3-Benzoylphenyl)-5-chloro-2-(4-chlorophenylsulfonylamino)benzamide
89) Methyl 4-(5-chloro-2-(4-chlorophenylsulfonylamino)benzoylamino)-2-methoxybenzoate
90) 5-Chloro-2-(4-chlorophenylsulfonylamino)-N-(2-carbamoylphenyl)benzamide
91) 5-Chloro-2-(4-chlorophenylsulfonylamino)-N-(4-carbamoylphenyl)benzamide
92) 5-Chloro-2-(4-chlorophenylsulfonylamino)-N-(3-carbamoyl-2-methoxyphenyl)benzamide
93) 5-Chloro-2-(4-chlorophenylsulfonylamino)-N-(3-diethylaminomethyl-4-hydroxyphenyl)benzamide
94) 5-Chloro-2-(4-chlorophenylsulfonylamino)-N-(2,5-diethoxy-4-(morpholin-4-yl)phenyl)benzamide
95) N-(3-Acetylaminophenyl)-5-chloro-2-(4-chlorophenylsulfonylamino)benzamide
96) 3-(4-(5-Chloro-2-(4-chlorophenylsulfonylamino)benzoylamino)phenyl)acrylic acid
97) 5-Chloro-2-(4-chlorophenylsulfonylamino)-N-(4-(cyanophenylmethyl)phenyl)benzamide
98) 5-Chloro-2-4-chlorophenylsulfonylamino)-N-(4-(ethyl(2-hydroxyethyl)amino)phenyl)benzamide
99) 5-Chloro-2-(4-chlorophenylsulfonylamino)-N-(2-(2,4-dichlorophenoxy)phenyl)benzamide
100) 5-Chloro-2-(4-chlorophenylsulfonylamino)-N-(2-oxo-2H-chromen-6-yl)benzamide
101) N-(4-(5-chloro-2-(4-chlorophenylsulfonylamino)benzoylamino)phenyl)oxamide
102) (4-(5-Chloro-2-(4-chlorophenylsulfonylamino)benzoylamino)benzoylamino)acetic acid
103) (4-(5-Chloro-2-(4-chlorophenylsulfonylamino)benzoylamino)phenyl)acetic acid
104) 3-(4-(5-Chloro-2-(4-chlorophenylsulfonylamino)benzoylamino)benzoylamino)propionic acid
105) (4-(5-Chloro-2-(4-chlorophenylsulfonylamino)benzoylamino)benzyl)-phosphonic acid
106) 4-(4-(5-Chloro-2-(4-chlorophenylsulfonylamino)benzoylamino)phenyl)butyric acid
107) 2-(4-(5-Chloro-2-(4-chlorophenylsulfonylamino)benzoylamino)benzoylamino)pentanedioic acid
108) (3-(5-Chloro-2-(4-chlorophenylsulfonylamino)benzoylamino)phenyl)acetic acid
109) 5-Chloro-2-(4-chlorophenylsulfonylamino)-N-(1H-indazol6-yl))benzamide
110) 5-Chloro-2-(4-chlorophenylsulfonylamino)-N-(quinolin-5-yl )benzamide
111) 5-Chloro-2-(4-chlorophenylsulfonylamino)-N-(quinolin-6-yl)benzamide

Pharmacological Investigations
Activation of Soluble Guanylate Cyclase

The activation of soluble guanylate cyclase (sGC), which catalyzes the conversion of guanosine triphosphate (GTP) to cyclic guanosine monophosphate (cGMP) and pyrophosphate, by the compounds according to the invention was quantified with the aid of an enzyme immunoassay (EIA) from Amersham. For this, the test substances were first incubated with sGC in microtiter plates and then the quantity of the resulting cGMP was determined.

The sGC employed had been isolated from bovine lung (see Methods in Enzymology, Volume 195, p. 377). The test solutions (100 μl per well) contained 50 mM triethanolamine (TEA) buffer (pH 7.5), 3 mM MgCl$_2$, 3 mM reduced glutathione (GSH), 0.1 mM GTP, 1 mM 3-isobutyl-1-methylxanthine (IBMX), suitably diluted enzyme solution and the test substance or, in the control experiments, solvent. The test substances were dissolved in dimethyl sulfoxide (DMSO) and the solution was diluted with DMSO/water such that the final concentration c of test substance in the test batch had the value indicated below. The DMSO concentration in the test batch was 5% (v/v). The reaction was started by addition of the sGC. The reaction mix was incubated at 37° C. for 15 to 20 minutes and then stopped by ice-cooling and addition of the stop reagent (50 mM EDTA, pH 8.0). An aliquot of 50 μl was taken and employed for the determination of the cGMP content using the acetylation protocol of the Amersham cGMP EIA kit. The absorption of the samples was measured at 450 nm (reference wavelength 620 nm) in a microtiter plate reading apparatus. The cGMP concentration was determined by means of a calibration curve, which was obtained under the same experimental conditions. The activation of the sGC by a test substance is indicated as n-fold stimulation of the basal enzyme activity which was found in the control experiments (with solvent instead of test substance) (calculated according to the formula n-fold stimulation=[cGMP]$_{test\ substance}$/[cGMP]$_{control}$).

The following results were obtained:

| Compound of Example No. | Concentration c (μM) | n-fold stimulation |
|---|---|---|
| 1 | 100 | 3.6 |
| 2 | 100 | 9.2 |
| 3 | 100 | 2 |
| 4 | 25 | 5.5 |
| 5 | 10 | 9.3 |
| 6 | 100 | 4.2 |
| 7 | 100 | 2.8 |
| 8 | 10 | 5.3 |
| 9 | 100 | 1.6 |
| 10 | 100 | 1.7 |
| 11 | 100 | 1.8 |
| 12 | 25 | 2.8 |
| 13 | 100 | 1.8 |
| 14 | 100 | 1.7 |
| 15 | 10 | 9.9 |
| 16 | 100 | 4.1 |
| 17 | 100 | 2 |
| 18 | 100 | 3.2 |
| 19 | 100 | 26.3 |
| 21 | 50 | 8 |
| 23 | 25 | 2.2 |
| 24 | 50 | 2.4 |
| 25 | 50 | 2.4 |
| 33 | 50 | 3.8 |
| 93 | 50 | 1.5 |
| 97 | 12.5 | 4.9 |
| 102 | 50 | 1.7 |
| 108 | 50 | 2.5 |
| 111 | 50 | 6.1 |

What is claimed is:

1. A method for activating soluble guanylate cyclase, which comprises administering to a host in need of the activation at least one compound of the formula I

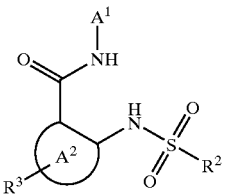

in any stereoisomeric form,
or a physiologically tolerable salt thereof,
in which $A^1$ is a radical from the group consisting of phenyl, naphthyl and heteroaryl, which can all be substituted by one or more identical or different radicals $R^1$;

the ring $A^2$, which includes the carbon atoms which carry the groups CO—NH—$A^1$ and NH—SO$_2$R$^2$, is a benzene ring, a naphthalene ring, a saturated or partially unsaturated 3-membered to 7-membered carbocycle, a saturated, partially unsaturated or aromatic monocyclic 5-membered to 7-membered heterocycle that contains one or more ring heteroatoms from the group consisting of N, O and S, or a saturated, partially unsaturated or aromatic bicyclic 8-membered to 10-membered heterocycle that contains one or more ring heteroatoms from the group consisting of N, O and S;

$R^1$ is halogen, aryl, CF$_3$, NO$_2$, OH, —O—(C$_1$–C$_7$)-alkyl, —O—(C$_2$–C$_4$)-alkyl-O—(C$_1$–C$_7$)-alkyl, —O-aryl, (C$_1$–C$_2$)-alkylenedioxy, NR$^5$R$^6$, CN, CO—NR$^5$R$^6$, COOH, CO—O—(C$_1$–C$_5$)-alkyl, heterocyclyl, CHO, CO—(C$_1$–C$_{10}$)-alkyl, CO-aryl or (C$_1$–C$_{10}$)-alkyl that can be substituted by one or more identical or different radicals $R^4$;

$R^2$ is aryl, heterocyclyl, NR$^5$R$^6$ or (C$_1$–C$_{10}$)-alkyl that can be substituted by one or more identical or different radicals $R^4$;

$R^3$ is one or more identical or different substituents from the group consisting of hydrogen, halogen, CF$_3$, OH, —O—(C$_1$–C$_{10}$)-alkyl, —O—(C$_1$–C$_7$)-alkyl-R$^7$, —O-aryl, SH, —S—(C$_1$–C$_{10}$)-alkyl, —S—(C$_1$–C$_7$)-alkyl-R$^7$, —S-aryl, (C$_1$–C$_3$)-alkylenedioxy, CN, NO$_2$, NR$^8$R$^9$, CO—NR$^5$R$^6$, COOH, CO—O—(C$_1$–C$_5$)-alkyl, heterocyclyl, S(O)$_n$—(C$_1$–C$_7$)-alkyl, S(O)$_n$-aryl, S(O)$_n$—NR$^5$R$^6$ and (C$_1$–C$_7$)-alkyl which can be substituted by one or more identical or different radicals $R^4$;

$R^4$ is fluorine, OH, —O—(C$_1$–C$_{10}$)-alkyl, —O—(C$_1$–C$_7$)-alkyl-R$^7$, —O-aryl, SH, —S—(C$_1$–C$_{10}$)-alkyl —S—(C$_1$–C$_7$)-alkyl-R$^7$, —S-aryl, —P(O)(O—(C$_1$–C$_5$)-alkyl)$_2$, —P(O)(OH)$_2$, CN, NR$^8$R$^9$, CO—NH$_2$, CO—NH—(C$_1$–C$_3$)-alkyl, CO—N((C$_1$–C$_3$)-alkyl)$_2$, COOH, CO—O—(C$_1$–C$_5$)-alkyl, heterocyclyl or oxo;

$R^5$ is hydrogen, (C$_1$–C$_{10}$)-alkyl which can be substituted by one or more identical or different substituents $R^4$ and/or by aryl, or is aryl, heterocyclyl, CO—(C$_1$–C$_{10}$)-alkyl, CO-aryl, CO-heterocyclyl, SO$_2$—(C$_1$–C$_{10}$)-alkyl, SO$_2$-aryl or SO$_2$-heterocyclyl;

$R^6$, independently of $R^5$, has one of the meanings indicated for $R^5$, or $R^5$ and $R^6$, together with the nitrogen atom to which they are bonded, form a 5-membered to 8-membered saturated or partially unsaturated ring which, in addition to the nitrogen atom carrying the groups $R^5$ and $R^6$, can also contain one or more further ring heteroatoms from the group consisting of N, O and S and which can be substituted by one or more identical or different substituents from the group consisting of fluorine, $(C_1-C_5)$-alkyl, $(C_1-C_3)$-hydroxyalkyl, —$(C_1-C_3)$-alkyl-O—$(C_1-C_4)$-alkyl, aryl, $CF_3$, OH, —O—$(C_1-C_7)$-alkyl, —O-aryl, —O—$(C_2-C_4)$-alkyl-O—$(C_1-C_7)$-alkyl, $(C_2-C_3)$-alkylenedioxy, $NR^8R^9$, CN, CO—$NH_2$, CO—NH—$(C_1-C_3)$-alkyl, CO—N$((C_1-C_3)$-alkyl$)_2$, COOH, CO—O—$(C_1-C_5)$-alkyl, CHO, CO—$(C_1-C_5)$-alkyl, $S(O)_n$—$(C_1-C_4)$-alkyl, $S(O)_n$—$NH_2$, $S(O)_n$—NH—$(C_1-C_3)$-alkyl, $S(O)_n$—N$((C_1-C_3)$-alkyl$)_2$, oxo, —$(CH_2)_m$—$NH_2$, —$(CH_2)_m$—NH—$(C_1-C_4)$-alkyl and —$(CH_2)_m$—N$((C_1-C_4)$-alkyl$)_2$, where in the substituent —$(CH_2)_m$—N$((C_1-C_4)$-alkyl$)_2$ the two alkyl groups can be linked by a single bond and then, together with the nitrogen atom carrying them, form a 5-membered to 7-membered ring which, in addition to the nitrogen atom and the carbon atoms, can additionally also contain an oxygen atom, a sulfur atom or a group $NR^5$ as a ring member;

$R^7$ is OH, —O—$(C_1-C_7)$-alkyl, $NH_2$, —NH—$(C_1-C_4)$-alkyl or —N$((C_1-C_4)$-alkyl$)_2$, where in the substituent N$((C_1-C_4)$-alkyl$)_2$ the two alkyl groups can be linked by a single bond and then, together with the nitrogen atom carrying them, form a 5-membered to 7-membered ring which, in addition to the nitrogen atom and the carbon atoms can additionally also contain an oxygen atom, a sulfur atom or a group $NR^5$ as a ring member;

$R^8$ is hydrogen or $(C_1-C_7)$-alkyl which can be substituted by one or more identical or different substituents from the group consisting of OH, —O—$(C_1-C_5)$-alkyl, $NH_2$, —NH—$(C_1-C_4)$-alkyl and —N$((C_1-C_4)$-alkyl$)_2$;

$R^9$, independently of $R^8$, has one of the meanings of $R^8$ or is CO—$(C_1-C_4)$-alkyl;

aryl is phenyl, naphthyl or heteroaryl, which can all be substituted by one or more identical or different substituents from the group consisting of halogen, $(C_1-C_5)$-alkyl, phenyl, tolyl, $CF_3$, $NO_2$, OH, —O—$(C_1-C_5)$-alkyl, —O—$(C_2-C_4)$-alkyl-O—$(C_1-C_3)$-alkyl, $(C_1-C_2)$-alkylenedioxy, $NH_2$, —NH—$(C_1-C_3)$-alkyl, —N$((C_1-C_3)$-alkyl$)_2$, NH—CHO, —NH—CO—$(C_1-C_5)$-alkyl, CN, CO—$NH_2$, CO—NH—$(C_1-C_3)$-alkyl, CO—N$((C_1-C_3)$-alkyl$)_2$, COOH, CO—O—$(C_1-C_5)$-alkyl, heterocyclyl, CHO, CO—$(C_1-C_5)$-alkyl, $S(O)_n$—$(C_1-C_4)$-alkyl, $S(O)_n$-phenyl, $S(O)_n$-tolyl, $S(O)_n$-$NH_2$, $S(O)_2$—NH—$(C_1-C_3)$-alkyl and $S(O)_2$—N$((C_1-C_3)$-alkyl$)_2$;

heteroaryl is the radical of a monocyclic 5-membered or 6-membered aromatic heterocycle or of a bicyclic 8-membered to 10-membered aromatic heterocycle, each of which contain one or more ring heteroatoms from the group consisting of N, O and S;

heterocyclyl is the radical of a monocyclic or polycyclic, 5-membered to 11-membered saturated or partially unsaturated heterocycle which contains one or more ring heteroatoms from the group consisting of N, O and S and which can be substituted by one or more identical or different substituents from the group consisting of fluorine, $(C_1-C_5)$-alkyl, OH, —O—$(C_1-C_5)$-alkyl, —O—$(C_2-C_4)$-alkyl-O—$(C_1-C_3)$-alkyl, $NH_2$, —NH—$(C_1-C_3)$-alkyl, —N$((C_1-C_3)$-alkyl$)_2$, CN, CO—$NH_2$, CO—NH—$(C_1-C_3)$-alkyl, CO—N$((C_1-C_3)$-alkyl$)_2$, COOH and CO—O—$(C_1-C_5)$-alkyl;

n is 0, 1 or 2; and m is 2, 3 or 4.

2. The method as claimed in claim 1, in which $A^1$ is phenyl, naphthyl or bicyclic heteroaryl, where these radicals can be unsubstituted or substituted.

3. The method as claimed in claim 1, in which $A^2$ together with the atoms carrying both the group $R^2$—$SO^2$—NH and the group CO-NH-$A^1$ forms an aromatic ring.

4. The method as claimed in claim 1, in which $R^2$ is unsubstituted or substituted aryl.

5. The method as claimed in claim 1, in which $A^2$ together with the atoms carrying both the group $R^2$—$SO_2$—NH and the group CO-NH-$A^1$ forms an unsubstituted or substituted benzene ring and $R^2$ is unsubstituted or substituted aryl.

6. The method as claimed in claim 1, which provides for the therapy in the host of a cardiovascular disorder, endothelial dysfunction, diastolic dysfunction, atherosclerosis, high blood pressure, angina pectoris, thrombosis, restenosis, myocardial infarct, stroke, cardiac insufficiency, pulmonary hypertension, erectile dysfunction, bronchial asthma, chronic renal insufficiency, diabetes or liver cirrhosis or which provides for improving a restricted learning capacity or memory power of the host.

7. A method as claimed in claim 1, wherein the radical $A^1$ is substituted by at least one radical $R^1$, wherein the at least one radical $R^1$ is —O-aryl, wherein aryl is unsubstituted or substituted as defined in claim 1.

8. A method as claimed in claim 11, wherein the at least one radical $R^1$ is —O-phenyl, wherein phenyl is unsubstituted or substituted as defined in claim 1.

9. A method for the therapy of a cardiovascular disorder, endothelial dysfunction, diastolic dysfunction, atherosclerosis, high blood pressure, angina pectoris, thrombosis, restenosis, myocardial infarct, stroke, cardiac insufficiency, pulmonary hypertension, erectile dysfunction, bronchial asthma, chronic renal insufficiency, diabetes or liver cirrhosis or which provides for improving a restricted learning capacity or memory power of the host, which comprises administering to a host in need of the therapy at least one compound of the formula I

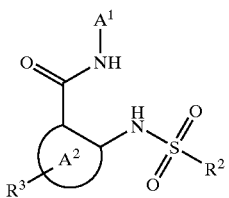

I in any stereoisomeric form,
or a physiologically tolerable salt thereof,
in which $A^1$ is a radical from the group consisting of phenyl, naphthyl and heteroaryl, which can all be substituted by one or more identical or different radicals $R^1$;

the ring $A^2$, which includes the carbon atoms which carry the groups CO—N H—$A^1$ and NH—$SO^2R^2$, is a benzene ring, a naphthalene ring, a saturated or partially unsaturated 3-membered to 7-membered carbocycle, a saturated, partially unsaturated or aromatic monocyclic 5-membered to 7-membered heterocycle that contains one or more ring heteroatoms from the group consisting of N, O and S, or a saturated, partially unsaturated or aromatic bicyclic 8-membered to 10-membered heterocycle that contains one or more ring heteroatoms from the group consisting of N, O and S;

$R^1$ is halogen, aryl, $CF_3$, $NO_2$, OH, —O—$(C_1-C_7)$-alkyl, —O—$(C_2-C_4)$-alkyl-O—$(C_1-C_7)$-alkyl, —O-aryl, $(C_1-C_2)$-alkylenedioxy, $NR^5R^6$, CN, CO—$NR^5R^6$, COOH, CO—O—$(C_1-C_5)$-alkyl, heterocyclyl, CHO, CO—$(C_1-C_{10})$-alkyl, CO-aryl or $(C_1-C_{10})$-alkyl which can be substituted by one or more identical or different radicals $R^4$;

$R^2$ is aryl, heterocyclyl, $NR^5R^6$ or $(C_1-C_{10})$-alkyl that can be substituted by one or more identical or different radicals $R^4$;

$R^3$ is one or more identical or different substituents from the group consisting of hydrogen, halogen, $CF_3$, OH, —O—$(C_1-C_{10})$-alkyl, —O—$(C_1-C_7)$-alkyl-$R^7$, —O-aryl, SH, —S—$(C_1-C_{10})$-alkyl, —S—$(C_1-C_7)$-alkyl-$R^7$, —S-aryl, $(C_1-C_3)$-alkylenedioxy, CN, $NO_2$, $NR^{NR5}R^6$, COOH, CO—O—$(C_1-C_5)$-alkyl, heterocyclyl, $S(O)_n$—$(C_1-C_7)$-alkyl, $S(O)_n$-aryl, $S(O)_n$—$NR^5R^6$ and $(C_1-C_7)$-alkyl that can be substituted by one or more identical or different radicals $R^4$;

$R^4$ is fluorine, OH, —O—$(C_1-C_{10})$-alkyl, —O—$(C_1-C_7)$-alkyl-$R^7$, —O-aryl, SH, —S—$(C_1-C_{10})$-alkyl, —S—$(C_1-C_7)$-alkyl-$R^7$, —S-aryl, —P(O)(O—$(C_1-C_5)$-alkyl$)_2$, —P(O)(OH$)_2$, CN, $NR^8R^9$, CO—$NH_2$, CO—NH—$(C_1-C_3)$-alkyl, CO—N$((C_1-C_3)$-alkyl$)_2$, COOH, CO—O—$(C_1-C_5)$-alkyl, heterocyclyl or oxo;

$R^5$ is hydrogen, $(C_1-C_{10})$-alkyl which can be substituted by one or more identical or different substituents $R^4$ and/or by aryl, or is aryl, heterocyclyl, CO—$(C_1-C_{10})$-alkyl, CO-aryl, CO-heterocyclyl, $SO_2$—$(C_1-C_{10})$-alkyl, $SO_2$-aryl or $SO_2$-heterocyclyl;

$R^6$, independently of $R^5$, has one of the meanings indicated for $R^5$, or $R^5$ and $R^6$, together with the nitrogen atom to which they are bonded, form a 5-membered to 8-membered saturated or partially unsaturated ring which, in addition to the nitrogen atom carrying the groups $R^5$ and $R^6$ can also contain one or more further ring heteroatoms from the group consisting of N, O and S and which can be substituted by one or more identical or different substituents from the group consisting of fluorine, $(C_1-C_5)$-alkyl, $(C_1-C_3)$-hydroxyalkyl, —$(C_1-C_3)$-alkyl-O—$(C_1-C_4)$-alkyl, aryl, $CF_3$, OH, —O—$(C_1-C_7)$-alkyl, —O-aryl, —O—$(C_2-C_4)$-alkyl-O—$(C_1-C_7)$-alkyl, $(C_2-C_3)$-alkylenedioxy, $NR^8R^9$, CN, CO—$NH_2$, CO—NH—$(C_1-C_3)$-alkyl, CO—N$((C_1-C_3)$-alkyl$)_2$, COOH, CO—O—$(C_1-C_5)$-alkyl, CHO, CO—$(C_1-C_5)$-alkyl, $S(O)_n$—$(C_1-C_4)$-alkyl, $S(O)_n$—$NH_2$, $S(O)_n$—NH—$(C_1-C_3)$-alkyl, $S(O)_n$—N$((C_1-C_3)$-alkyl$)_2$,oxo —$(CH_2)_m$—$NH_2$, —$(CH_2)_m$—NH—$(C_1-C_4)$-alkyl and —$(CH_2)_m$—N$((C_1-C_4)$-alkyl$)_2$, where in the substituent —$(CH_2)_m$—N$((C_1-C_4)$-alkyl$)_2$ the two alkyl groups can be linked by a single bond and then together with the nitrogen atom carrying them form a 5-membered to 7-membered ring which in addition to the nitrogen atom and the carbon atoms, can additionally also contain an oxygen atom, a sulfur atom or a group $NR^5$ as a ring member;

$R^7$ is OH, —O—$(C_1-C_7)$-alkyl, $NH_2$, —NH—$(C_1-C_4)$-alkyl or —N$((C_1-C_4)$-alkyl$)_2$, where in the substituent N$((C_1-C_4)$-alkyl$)_2$ the two alkyl groups can be linked by a single bond and then together with the nitrogen atom carrying them form a 5-membered to 7-membered ring which, in addition to the nitrogen atom and the carbon atoms, can additionally also contain an oxygen atom, a sulfur atom or a group $NR^5$ as a ring member;

$R^8$ is hydrogen or $(C_1-C_7)$-alkyl which can be substituted by one or more identical or different substituents from the group consisting of OH, —O—$(C_1-C_5)$-alkyl, $NH_2$, —NH—$(C_1-C_4)$-alkyl and —N$((C_1-C_4)$-alkyl$)_2$;

$R^9$, independently of $R^8$, has one of the meanings of $R^8$ or is CO—$(C_1-C_4)$-alkyl;

aryl is phenyl, naphthyl or heteroaryl, which can all be substituted by one or more identical or different substituents from the group consisting of halogen, $(C_1-C_5)$-alkyl, phenyl, tolyl, $CF_3$, $NO_2$, OH, —O—$(C_1-C_5)$-alkyl, —O—$(C_2-C_4)$-alkyl-O—$(C_1-C_3)$-alkyl, $(C_1-C_2)$-alkylenedioxy, $NH_2$, —NH—$(C_1-C_3)$-alkyl, —N$((C_1-C_3)$-alkyl$)_2$, NH—CHO, —NH—CO—$(C_1-C_5)$-alkyl, CN, CO—$NH_2$, CO—NH—$(C_1-C_3)$-alkyl, CO—N$((C_1-C_3)$-alkyl$)_2$, COOH, CO—O—$(C_1-C_5)$-alkyl, heterocyclyl, CHO, CO—$(C_1-C_5)$-alkyl, $S(O)_n$—$(C_1-C_4)$-alkyl, $S(O)_n$-phenyl, $S(O)_n$-tolyl, $S(O)_2$—$NH_2$, $S(O)_2$—NH—$(C_1-C_3)$-alkyl and $S(O)_2$—N$((C_1-C_3)$-alkyl$)_2$;

heteroaryl is the radical of a monocyclic 5-membered or 6-membered aromatic heterocycle or a bicyclic 8-membered to 10-membered aromatic heterocycle, each of which contain one or more ring heteroatoms from the group consisting of N, O and S;

heterocyclyl is the radical of a monocyclic or polycyclic, 5-membered to 11-membered saturated or partially unsaturated heterocycle which contains one or more ring heteroatoms from the group consisting of N, O and S and which can be substituted by one or more identical or different substituents from the group consisting of fluorine, $(C_1-C_5)$-alkyl, OH, —O—$(C_1-C_5)$-alkyl, —O—$(C_2-C_4)$-alkyl-O—$(C_1-C_3)$-alkyl, $NH_2$, —NH—$(C_1-C_3)$-alkyl, —N$((C_1-C_3)$-alkyl$)_2$, CN, CO—$NH_2$, CO—NH—$(C_1-C_3)$-alkyl, CO—N$((C_1-C_3)$-alkyl$)_2$, COOH and CO—O—$(C_1-C_5)$-alkyl;

n is 0, 1 or 2; and m is 2, 3 or 4.

\* \* \* \* \*

UNITED STATES PATENT AND TRADEMARK OFFICE
CERTIFICATE OF CORRECTION

PATENT NO. : 6,809,089 B2
DATED : October 26, 2004
INVENTOR(S) : Ursula Schindler et al.

It is certified that error appears in the above-identified patent and that said Letters Patent is hereby corrected as shown below:

Title page,
Item [74], *Attorney, Agent or Firm*, "Fennigan" should read -- Finnegan --.

Column 28,
Line 61, "which" should read -- that --.

Column 30,
Line 9, "$R^2$-$SO^2$-NH" should read -- $R^2$-$SO_2$-NH --.
Line 61, "CO-N H-$A^1$" should read -- CO-NH-$A^1$ --.
Line 61, "NH-$SO^2$-$R^2$" should read -- NH-$SO_2$-$R^2$ --.

Column 31,
Line 19, after "$NO_2$" insert -- $NR^8R^9$, CO- --.
Line 20, "$NR^{NR5}R^6$, CO-" should read -- $NR^5$-$R^6$ --.
Line 32, "which" should read -- that --.

Column 32,
Line 37, "or a" should read -- or of a --.

Signed and Sealed this

Seventeenth Day of May, 2005

JON W. DUDAS
*Director of the United States Patent and Trademark Office*